US011194294B2

(12) United States Patent
Raymann et al.

(10) Patent No.: US 11,194,294 B2
(45) Date of Patent: Dec. 7, 2021

(54) SCHEDULING DEVICE FOR CUSTOMIZABLE ELECTRONIC NOTIFICATIONS

(71) Applicant: Apple Inc., Cupertino, CA (US)

(72) Inventors: Roy J. E. M. Raymann, Campbell, CA (US); Jay Kriz Blahnik, San Francisco, CA (US); Stephanie M. Greer, San Francisco, CA (US); Aroon Pahwa, Palo Alto, CA (US); Jonathan T. Varbel, San Jose, CA (US); Kevin M. Lynch, Woodside, CA (US)

(73) Assignee: Apple Inc., Cupertino, CA (US)

( * ) Notice: Subject to any disclaimer, the term of this patent is extended or adjusted under 35 U.S.C. 154(b) by 706 days.

(21) Appl. No.: 16/019,407

(22) Filed: Jun. 26, 2018

(65) Prior Publication Data

US 2018/0307185 A1 Oct. 25, 2018

Related U.S. Application Data

(63) Continuation of application No. 15/838,035, filed on Dec. 11, 2017, now Pat. No. 10,054,909, which is a
(Continued)

(51) Int. Cl.
*G04F 3/06* (2006.01)
*G04G 9/00* (2006.01)
(Continued)

(52) U.S. Cl.
CPC ............ *G04F 3/06* (2013.01); *A61B 5/4812* (2013.01); *A61B 5/4815* (2013.01); *A61B 5/742* (2013.01);
(Continued)

(58) Field of Classification Search
CPC .................................................. G04G 21/025
See application file for complete search history.

(56) References Cited

U.S. PATENT DOCUMENTS

| 2001/0048639 A1 | 12/2001 | Davidson |
| 2002/0080035 A1 | 6/2002 | Youdenko |
(Continued)

FOREIGN PATENT DOCUMENTS

| CN | 104053397 A | 9/2014 |
| CN | 104735264 A | 6/2015 |
(Continued)

OTHER PUBLICATIONS

International Preliminary Report on Patentability dated Dec. 20, 2018 in International Application No. PCT/US2017/031251. 9 pages.
(Continued)

*Primary Examiner* — Edwin A. Leon
*Assistant Examiner* — Jason M Collins
(74) *Attorney, Agent, or Firm* — Kilpatrick Townsend & Stockton

(57) ABSTRACT

Sleep alerts associated with an alarm can be scheduled using a first electronic device. Once scheduled, data can be collected from a second electronic device. This data can be used to determine an appropriate device, other than the first electronic device, at which the sleep alert can be presented. Once determined, the information can be sent to the appropriate device for presenting the sleep alert.

20 Claims, 18 Drawing Sheets

Related U.S. Application Data continuation of application No. 15/273,388, filed on Sep. 22, 2016, now Pat. No. 9,869,973.

(60) Provisional application No. 62/348,665, filed on Jun. 10, 2016.

(51) Int. Cl.
| | | |
|---|---|---|
| *G04G 13/02* | (2006.01) | |
| *G04G 21/02* | (2010.01) | |
| *G06F 9/451* | (2018.01) | |
| *G06Q 10/10* | (2012.01) | |
| *G06F 3/0484* | (2013.01) | |
| *G06Q 50/22* | (2018.01) | |
| *A61B 5/00* | (2006.01) | |
| *A61B 5/0205* | (2006.01) | |
| *A61B 5/282* | (2021.01) | |

(52) U.S. Cl.
CPC ........... *G04G 9/0064* (2013.01); *G04G 13/02* (2013.01); *G04G 21/025* (2013.01); *G06F 3/04847* (2013.01); *G06F 9/451* (2018.02); *G06Q 10/109* (2013.01); *G06Q 50/22* (2013.01); *A61B 5/0205* (2013.01); *A61B 5/282* (2021.01); *A61B 5/681* (2013.01)

(56) References Cited

U.S. PATENT DOCUMENTS

| | | | |
|---|---|---|---|
| 2007/0279234 A1 | 12/2007 | Walsh | |
| 2008/0150959 A1 | 6/2008 | Marui | |
| 2008/0234785 A1 | 9/2008 | Nakayama et al. | |
| 2010/0139722 A1 | 6/2010 | Koch et al. | |
| 2011/0230790 A1 | 9/2011 | Kozlov | |
| 2012/0092171 A1 | 4/2012 | Hwang et al. | |
| 2013/0018284 A1 | 1/2013 | Kahn et al. | |
| 2013/0027412 A1 | 1/2013 | Roddy | |
| 2013/0163394 A1 | 6/2013 | Loree, IV | |
| 2014/0210626 A1 | 7/2014 | Kresser et al. | |
| 2014/0269224 A1 | 9/2014 | Huh et al. | |
| 2014/0347366 A1* | 11/2014 | Emori | A61B 5/742 345/440 |
| 2016/0022202 A1* | 1/2016 | Peterson | G04G 13/023 368/251 |
| 2016/0217672 A1 | 7/2016 | Yoon et al. | |
| 2017/0031325 A1* | 2/2017 | Price | G04G 13/026 |
| 2017/0238864 A1 | 8/2017 | Raymann et al. | |
| 2017/0364037 A1* | 12/2017 | Liu | G04G 13/02 |
| 2018/0081324 A1* | 3/2018 | Sharoni | G04G 13/021 |

FOREIGN PATENT DOCUMENTS

| | | |
|---|---|---|
| CN | 105068414 A | 11/2015 |
| JP | 2011107111 A | 6/2011 |
| WO | 2004/032715 A2 | 4/2004 |
| WO | 2009/030882 A2 | 3/2009 |

OTHER PUBLICATIONS

International Preliminary Report on Patentability dated Dec. 20, 2018 in International Application No. PCT/US2017/031249. 15 pages.
Notification of the First Office Action dated Jun. 5, 2019 in Chinese Patent Application No. 201780033177.3. 10 pages, includes English translation.
Notice of Allowance dated Dec. 14, 2018 in U.S. Appl. No. 15/273,865. 10 pages. (copy not provided).
Notification of the First Office Action dated Oct. 11, 2019 in Chinese Patent Application No. 201780033394.2. 10 pages, includes English translation.
Non-Final Office Action dated Jul. 3, 2018 in U.S. Appl. No. 15/273,865. 11 pages. (copy not provided).
Notice of Allowance dated Mar. 9, 2018 in U.S. Appl. No. 15/838,035. 10 pages. (copy not provided).
Samsung Newsroom, "Track, Manage, Improve: Better Health with S Health App", Published on Wednesday, May 13, 2015; accessed on May 31, 2016; 13 pages, https://news.samsung.com/global/track-manage-improve-better-health-with-s-health-app. (copy not included).
Invitation to Pay Additional Fees dated Jul. 13, 2017 in International Application No. PCT/US2017/031249. 27 pages. (copy not included).
International Search Report and Written Opinion dated Aug. 28, 2017 in International Application No. PCT/US2017/031251. 16 pages. (copy not included).
International Search Report and Written Opinion dated Oct. 2, 2017 in International Application No. PCT/US2017/031249. 24 pages. (copy not included).
IBlog Apple, "20 Hidden Features of iOS 10 You Might Not Know About." Jun. 15, 2016. 9 pages. (copy not included).
Notice of Allowance dated Sep. 13, 2017 in U.S. Appl. No. 15/273,388. 9 pages. (copy not included).
First Action Interview Pilot Program Pre-Interview Communication dated Jan. 12, 2018 in U.S. Appl. No. 15/838,035. 3 pages. (copy not provided).
Decision to Grant dated Jan. 10, 2020, in Chinese Patent Application No. ZL201780033177.3. 7 pages (English translation of allowed claims only).
Decision to Grant dated Mar. 24, 2020, in Chinese Patent Application No. ZL201780033394.2. 5 pages (English translation of allowed claims only).

* cited by examiner

SCHEDULING DEVICE FOR CUSTOMIZABLE ELECTRONIC NOTIFICATIONS

CROSS-REFERENCES TO RELATED APPLICATIONS

This application is a continuation of U.S. application Ser. No. 15/838,035 entitled "Scheduling Device for Customizable Electronic Notifications," filed on Dec. 11, 2017, which is a continuation of U.S. application Ser. No. 15/273,388 entitled "Scheduling Device for Customizable Electronic Notifications," filed on Sep. 22, 2016, which claims the benefit of priority of U.S. Provisional Application Ser. No. 62/348,665, filed Jun. 10, 2016, entitled "Scheduling Device for Customizable Electronic Notifications." The disclosure of this application is incorporated herein by reference in its entirety.

This application is related to and incorporates by reference for all purposes the full disclosure of co-pending International Application No. PCT/US2017/031249 entitled "Scheduling Customizable Electronic Notifications," filed May 5, 2017, which is a continuation of U.S. application Ser. No. 15/273,865 entitled "Scheduling Customizable Electronic Notifications," filed Sep. 23, 2016 which claims the benefit of priority of U.S. Provisional Application Ser. No. 62/348,648 entitled "Scheduling Customizable Electronic Notifications" filed Jun. 10, 2016.

BACKGROUND

Sleeping is an activity that all people share, and recently more and more information is becoming available about the positive impacts that consistent sleep habits can have on one's health. Electronic devices such as mobile phones, media players, and the like may offer alarm clock applications capable of scheduling alarms similar to conventional alarm clocks. Each alarm clock application may have its own unique method for scheduling an alarm and otherwise interacting with the alarm clock application. Additionally, in recent years, specialized electronic devices and applications have been developed that can track aspects of one's sleep habits. Such devices, however, can be cost prohibitive to most people, or otherwise difficult to operate. This can lead to limited adoption of such specialized devices, or at least limited ongoing use.

BRIEF SUMMARY

Embodiments of the present disclosure can provide systems, computer-implemented methods, and computer-readable medium for interacting with a sleep alarm. According to one embodiment, a method may be implemented by a computer system to present, at least in response to a first user input, an alarm graphical user interface on a device. The alarm graphical user interface may include a generic alarm selector that, when selected, enables interaction with one or more generic alarms. The alarm graphical user interface may also include a sleep alarm selector that, when selected, enables interaction with a sleep alarm. The method may also include receiving a second user input that identifies selection of the sleep alarm selector. The method may also include presenting, at least in response to the second user input, a sleep alarm view of the alarm graphical user interface on the device. The method may also include receiving sleep configuration information. The method may also include determining, based at least in part on the sleep configuration information, a first future time corresponding to a suggested bedtime. The method may also include presenting, on the device, a sleep alert based at least in part on the first future time.

According to one embodiment, a computerized system may include a memory configured to store computer-executable instructions, an input component, a processor in communication with the memory configured to execute the computer-executable instructions, and a display. The display may present, in response to a first user input, a graphical user interface. The graphical user interface may include a first graphical user interface element that, when selected, enables interaction with one or more generic alarms. The graphical user interface may also include a second graphical user interface element that, when selected, enables interaction with a sleep alarm. The display may also present a sleep alarm view for scheduling the sleep alarm that presents an adjustable alarm indicator. The adjustable alarm indicator may include a first future time indication corresponding to a suggested bedtime and a second future time indication for triggering a wakeup alert of the sleep alarm.

According to one embodiment, a method may be implemented by a computer system to at least provide a graphical user interface for presentation at a user device. The graphical user interface may include a first user interface element corresponding to a sleep alarm and a second user interface element corresponding to a generic alarm. The method may also include receiving, from the user device, a first communication indicating selection of the first user interface element of the graphical user interface corresponding to the sleep alarm. The method may also include providing a sleep alarm view of the graphical user interface for presentation at the user device. The method may also include receiving configuration information generated based at least in part on interaction with the sleep alarm view. The method may also include scheduling, based at least in part on the configuration information, a wakeup alert to be presented at a first future time. The method may also include scheduling, based at least in part on the first future time and the configuration information, a sleep alert to be presented at a second future time occurring prior to the first future time.

According to one embodiment, a method may be implemented by a computer system to at least present a user interface including generic alarm option and a sleep alarm option. The method may also include presenting a first view including generic alarm related options when the generic alarm option is selected. The method may also include presenting a second view including sleep alarm related alarm options when the sleep alarm option is selected.

According to one embodiment, a computerized system may include a memory configured to store computer-executable instructions, an input component, a processor in communication with the memory configured to execute the computer-executable instructions, and a display. The display may present a sleep alarm view of a graphical user interface during a scheduling phase of an alarm setting sequence in response to a first input received at the input component. The sleep alarm view may present an adjustable alarm indicator located in a first region of the sleep alarm view and a sleep graph located in a second region of the graphical sleep alarm view. The adjustable alarm indicator may include a variable element having a variable annular shape including a first independently adjustable element associated with a suggested bedtime and a second adjustable element associated with an alarm time. The second adjustable element may be moveable to cause the first adjustable element and the second adjustable element to move dependently. The sleep graph may include one or more linear indicators, each corresponding to an interval and indicating an amount of time slept during the interval and a sleep range corresponding to a period and including an earliest bedtime and a latest wake time.

According to one embodiment, a method may be implemented by a computer system to at least receive a first input a device to initiate an alarm setting sequence. The method may also include, during the alarm setting sequence, presenting an adjustable alarm indicator located in a first region of a sleep alarm view of a graphical user interface. The adjustable alarm indicator may include a variable element having a variable annular shape, a bedtime element associated with a first end of the variable element and representing a suggested bedtime, and a wake time element associated with a second end of the variable element and representing a scheduled time for an alarm. Rotation of the bedtime element may adjust the suggested bedtime and cause the variable element to have a larger variable annular shape or a smaller variable annular shape. Rotation of the wake time element may adjust the scheduled time and the suggested bedtime and cause the variable element, the bedtime element, and the wake time element to rotate relative to a portion of the variable element.

According to one embodiment, a method may be implemented by a computer system to at least provide a user interface for presentation at a user device. The user interface may include an adjustable alarm indicator located in a first region of the user interface, and a sleep graph located in a second region of the user interface. The adjustable alarm indicator may include at least two variable ends corresponding to a first time and a second time, respectively. The sleep graph may include one or more linear indicators and a sleep range. Each linear indicator may correspond to an interval indicating an amount of time slept during the interval and may be generated based at least in part on sleep data. The sleep range may correspond to a period and include an earliest bedtime and a latest wake time for the period. The method may also include receiving, from the user device, a first communication indicating an adjustment to the first time. The method may also include determining that the adjustment results in the first time falling outside the sleep range including the earliest bedtime and the latest wake time. The method may also include generating an updated sleep graph that includes an updated sleep range for the period and that includes at least one of an updated earliest bedtime or an updated latest wake time. The method may also include providing the updated sleep graph for presentation at the user device.

DETAILED DESCRIPTION

Figure 1:
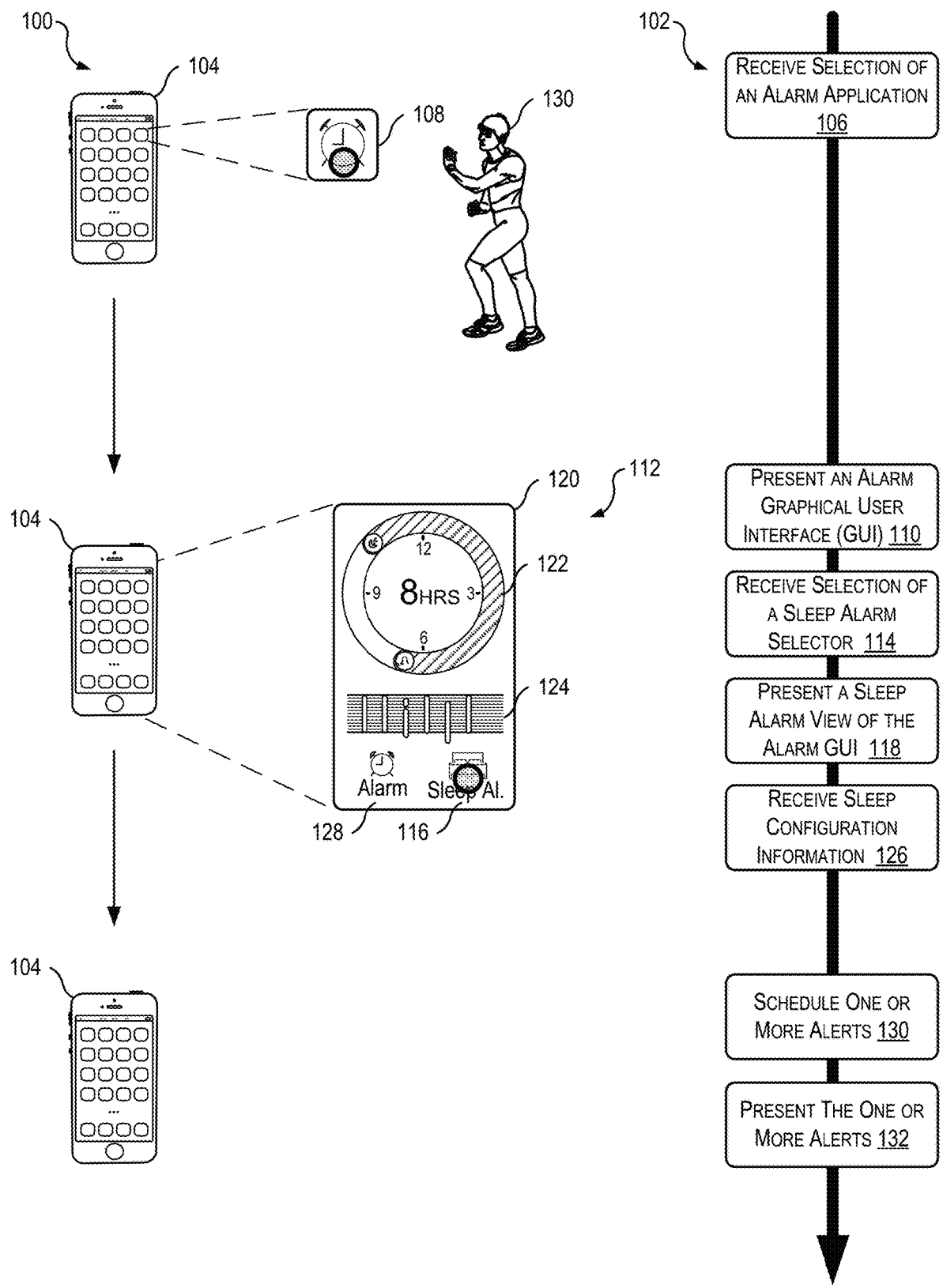
FIG. 1 illustrates a simplified block diagram depicting an example flow for interacting with a sleep alarm as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, and computer-readable media for interacting with a sleep alarm provided on an electronic device. In particular, this can include presenting the sleep alarm in a manner that enables ease of access and ease of scheduling. For example, an alarm application or clock application can be provided that historically includes an option for interacting with a generic alarm. In some examples, existing users of the alarm application may be accustomed to accessing the generic alarm in the alarm application. Thus, it may be desirable to add the sleep alarm and its attendant functionality to the existing alarm application adjacent to the generic alarm. The sleep alarm may also be included in its own application.

The sleep alarm described herein may improve the functioning of a user device on which the sleep alarm operates. For example, the sleep alarm may enable additional alarm options as compared to other alarm applications. These sleep alarm options may include scheduling and presenting a sleep alert (e.g., a sleep notification) prior to a suggested bedtime, scheduling and presenting a wake alert (e.g., a wake notification) at a scheduled wake time, and other similar options. The alarm application may also use actual sleep data associated with a user to customize the scheduling of these alerts. The sleep data may also be presented to the user in a way that assists the user improve and/or maintain health sleep habits.

When the sleep alarm is included in the alarm application, the sleep alarm may be presented as a sleep alarm view of an alarm graphical user interface. The sleep alarm view may include a combination of user interface elements for presenting information and receiving inputs. For example, the view may include an adjustable alarm indicator that has an annular (e.g., ring) shape. The adjustable alarm indicator may graphically represent aspects of the sleep alarm. For example, the adjustable alarm indicator may represent a suggested bedtime, a scheduled time for a wakeup alert, and a sleep duration corresponding to the suggested bedtime and the scheduled time for the wakeup alert. Elements of the adjustable alarm indicator may be independently and/or dependently adjustable to adjust the suggested bedtime, the scheduled time for the wakeup alert, and the sleep duration. The sleep alarm may also include functionality to schedule and present a sleep alert prior to the suggested bedtime. This sleep alert may prompt the user to begin her bedtime routine in order to be in bed and asleep at the suggested bedtime. The sleep alarm view may also include a sleep graph that represents historical sleep data for a particular period. The sleep data may be represented as a set of linear indicators, each indicating a sleep interval, a beginning of the sleep interval, an end of the sleep interval, and any recorded interruptions during the sleep interval. The sleep graph, including the linear indicators, may enable to user to graphically evaluate her sleep routine in terms of consistency (e.g., retiring and rising at similar times each day), sleep amount (e.g., how many total hours "in bed" or asleep), and interruptions (e.g., times during night when she was not asleep).

Turning now to the figures, FIG. 1 illustrates a simplified block diagram 100 depicting an example process 102 for interacting with a sleep alarm, according to at least one example. The diagram 100 can include a user device 104. The user device 104 may be any suitable electronic device such as a mobile phone, a media player, a tablet device, a personal computer, and the like. The process 102 may begin at 106 by the user device 104 receiving selection of an alarm (e.g., clock) application 108 by a user 130. The selection (e.g., as illustrated by an enclosed circular element with dimpled hatching) of the alarm application 108 may be received at an input device of the user device 104 such as a touchscreen or other suitable input device. In response to the selection at 106, the process 102 may include, at 110, presenting an alarm graphical user interface 112. The alarm graphical user interface 112 may be presented on the user device 104. The alarm graphical user interface 112 can include one or more views corresponding to alarms, clocks, and timers. For example, a first view may correspond to a world clock option, a second view may correspond to a generic alarm option, a third view may correspond to a sleep alarm option, a fourth view may correspond to a stopwatch option, a fifth view may correspond to a timer option, and so on and so forth.

At 114, the process 102 may include receiving selection of a sleep alarm selector 116. The selection of the sleep alarm selector 116 at 114 may be received at the input device of the user device 104. The sleep alarm selector 116 may be presented together with a generic alarm selector 128. Selection of the generic alarm selector 128 may cause presentation of a generic alarm view of the alarm graphical user interface 112.

In response to the selection at 114, the process 102 may include, at 118, presenting a sleep alarm view 120 of the alarm graphical user interface 112. The sleep alarm view 120 may include an adjustable sleep alarm indicator 122 and a sleep graph 124. The sleep alarm view 120 may be used to schedule aspects of a sleep alarm, including a sleep alert and a wakeup alert, and to implement other techniques relating to interacting with sleep alarms, as described herein. In some examples, elements of the adjustable sleep alarm indicator 122 may be moveable, rotatable, or otherwise adjustable as part of scheduling the sleep alarm. For example, at 126, the process 102 may include receiving sleep configuration information. In some examples, at least a portion of the sleep configuration information may be received via interactions (e.g., movements, rotations, adjustments, inputs, etc.) with the adjustable sleep alarm indicator 122.

At 130, the process 102 may include scheduling one or more alerts. This can include scheduling a sleep alert to go off at a first future time prior to a bedtime and scheduling a wakeup alert to go off at a second future time at a wake time. The first future time may be computed as an offset from a suggested bedtime and/or may be based at least in part on the sleep configuration information received at 126. The second future time may also be based at least in part on the sleep configuration information received at 126.

At 132, the process 102 may include presenting the one or more alerts. The sleep alert can be presented at the user device 104 in any suitable manner. The wakeup alert can also be presented at the user device 104 in any suitable manner. In some examples, the one or more alerts may be presented and/or executed on other user devices, certain electronic devices, and the like. For example, an alert may be presented by instructing a network-enabled light fixture to slowly increase in intensity. This is in addition to or in place of causing an audible sound to be output by the user device 104.

Figure 2:
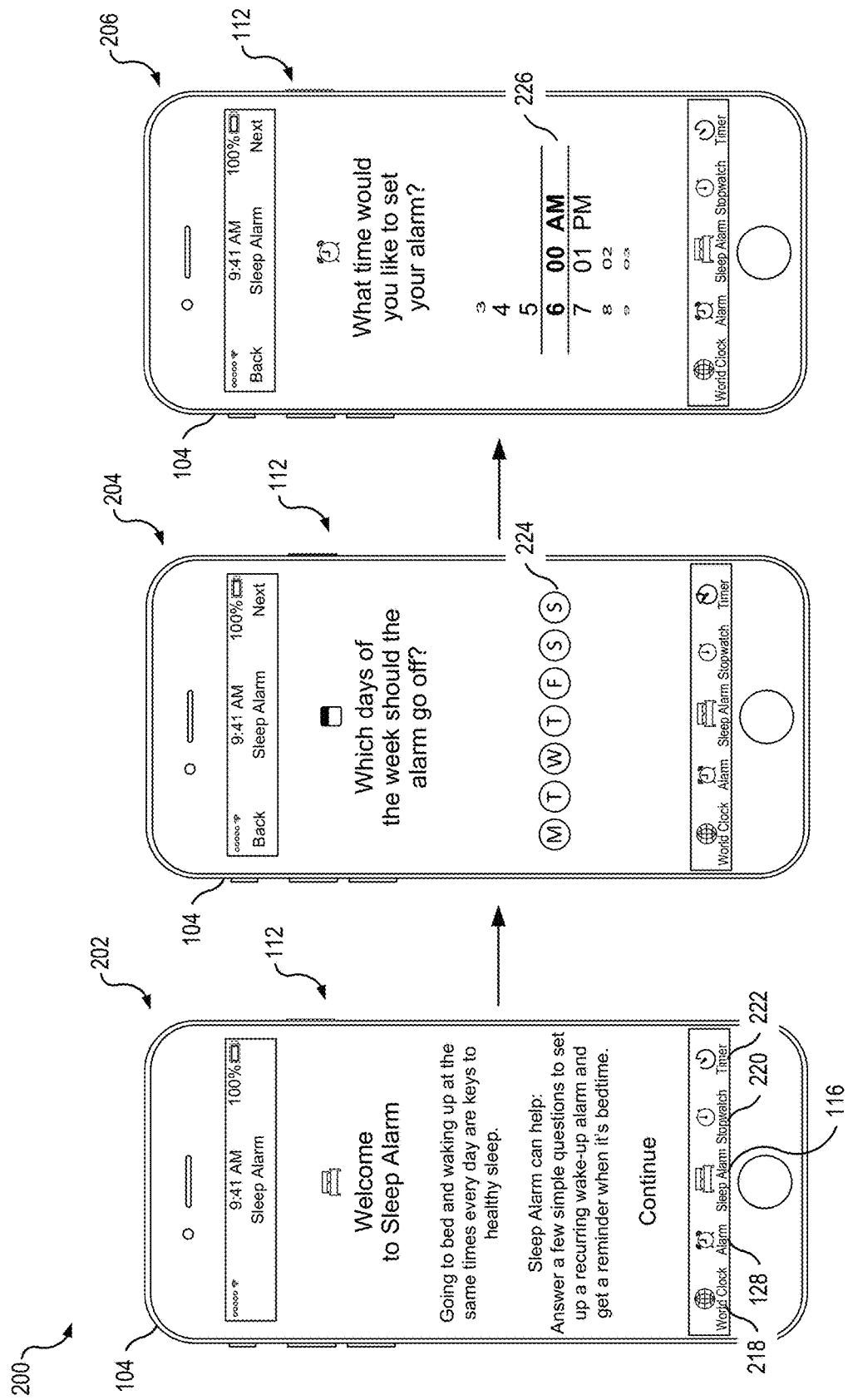
FIG. 2 illustrates example views of an alarm graphical user interface on a user device for interacting with a sleep alarm as described herein, according to at least one example.
Figure 3:
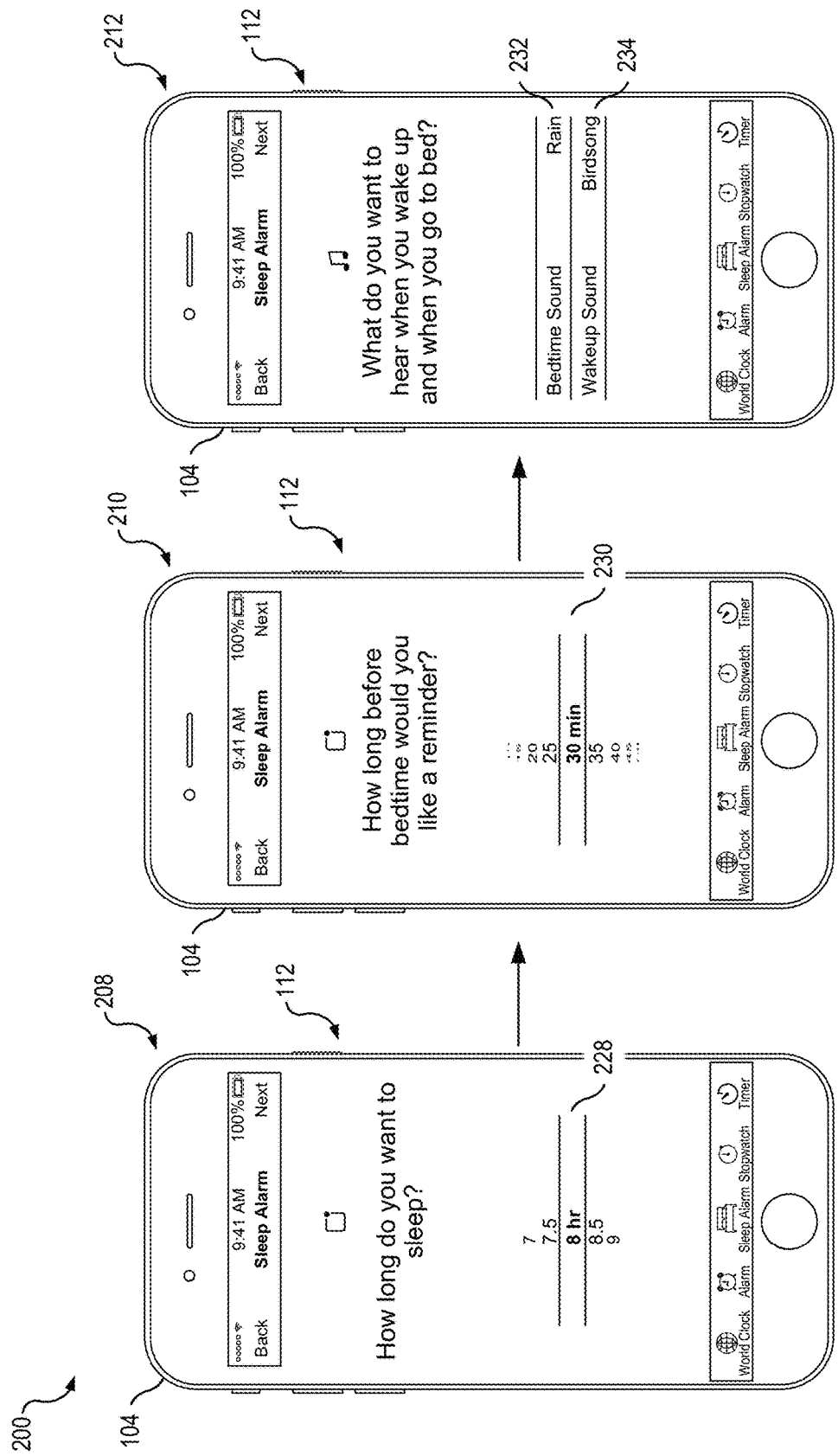
FIG. 3 illustrates example views of an alarm graphical user interface on a user device for interacting with a sleep alarm as described herein, according to at least one example.
Figure 4:
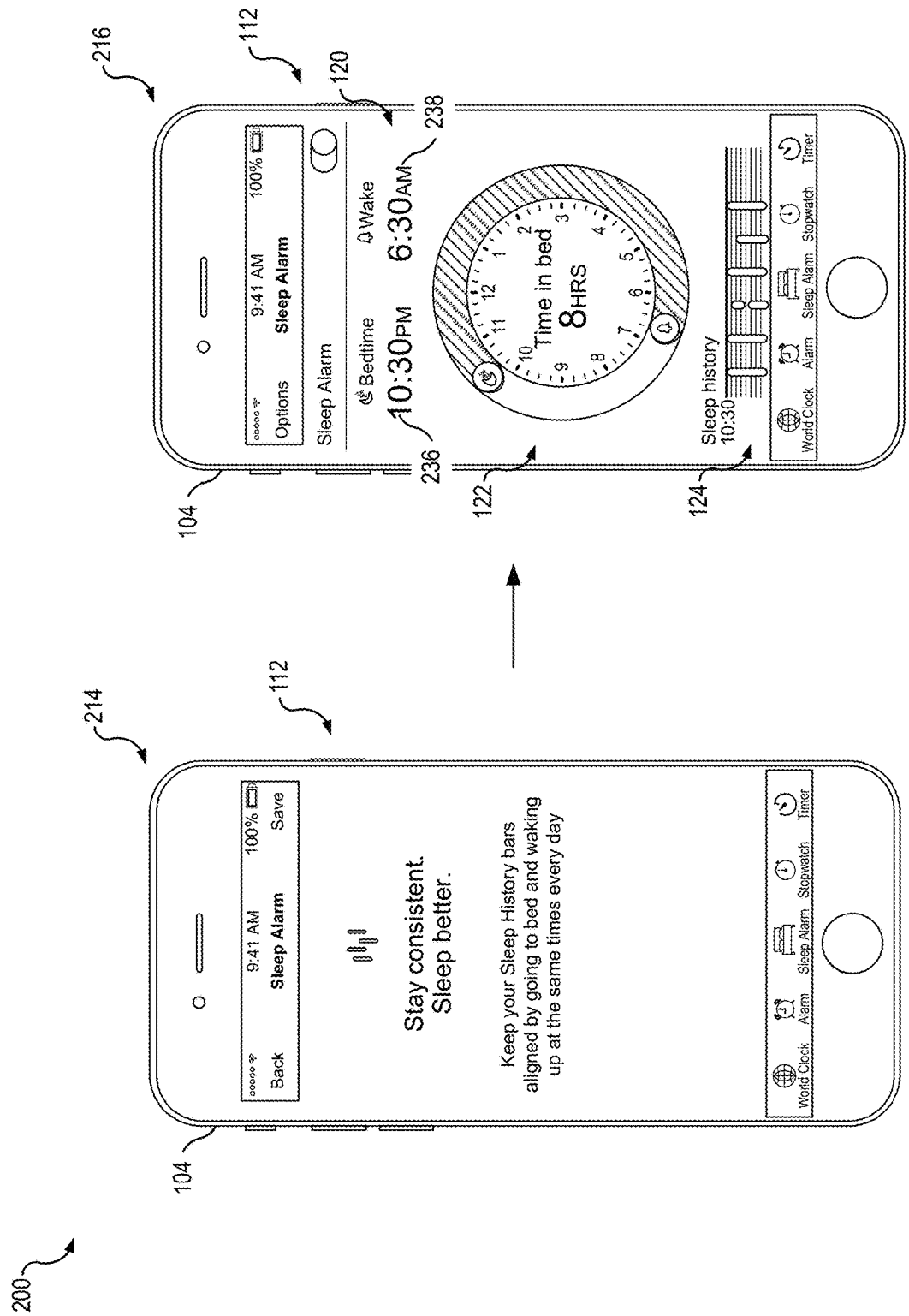
FIG. 4 illustrates example views of an alarm graphical user interface on a user device for interacting with a sleep alarm as described herein, according to at least one example.

FIGS. 2-4 illustrate the user device 104 including initial configuration views 202-216 of a configuration flow 200 depicting user interface elements relating to interacting with a sleep alarm, according to at least one example. Specifically, the initial configuration views 202-216 are examples of views of the alarm graphical user interface 112 that may be presented on a display of the user device 104. As described herein, the display of the user device 104 can be touch sensitive and/or pressure sensitive. In this manner, the display can function as an input component for receiving user input. Thus, the initial configuration views 202-216 (and other views described herein) are examples of views of a user interface that may be suitable for presentation on a touch sensitive and/or pressure sensitive display of the user device 104. It should be understood, however, that the initial configuration views 202-216 (and other views described herein) may be adapted for displays that are not touch sensitive and/or pressure sensitive. The initial configuration views 202-216 may be presented prior to an initial presentation of the sleep alarm view 120. The initial configuration views 202-216 may function to guide the user 130 through a configuration phase of an alarm setting sequence in order to configure aspects of a sleep alarm. Thus, using some initial configuration views 202-216, the user 130 may be presented with information about the sleep alarm, benefits of sleep, and/or any other suitable information pertaining to the sleep alarm. In some examples, using some initial configuration views 202-216, users may input information used to configured aspects of the sleep alarm and/or other alarms. In some examples, the initial configuration views 202-216 are presented periodically such that the user 130 can reevaluate her sleep routine.

As illustrated with reference to the initial configuration view 202, the alarm graphical user interface 112 may include, a clock selector 218, the generic alarm selector 128, the sleep alarm selector 116, a stopwatch selector 220, and a timer selector 222. The selectors may be presented as tabs along a bottom portion of the alarm graphical user interface 112. Selection of any of the clock selector 218, the generic alarm selector 128, the sleep alarm selector 116, the stopwatch selector 220, or the timer selector 222, may cause presentation of a different view of the alarm graphical user interface 112. For example, selection of the clock selector 218 may cause presentation of a clock view that includes one or more clocks corresponding to one or more time zones. Selection of the generic alarm selector 128 may cause presentation of a generic alarm view that includes one or more generic alarms, which may be used to schedule the generic alarms. Selection of the sleep alarm selector 116 may cause presentation of the sleep alarm view 120, as described in detail herein. Selection of the stopwatch selector 220 may cause presentation of a stopwatch view that includes stopwatch functionality. Selection of the timer selector 222 may cause presentation of a timer view that includes one or more timers, which may be used to schedule the timers.

Turning now to the initial configuration views 202-216 in more detail, the initial configuration view 202 may represent a welcome view. The welcome view can include information about the functionality of the sleep alarm and the benefits of sleep.

The initial configuration view 204 may be presented in response to user input with the initial configuration view 202 of the alarm graphical user interface 112. For example, the user 130 may select "Continue" or the view may change in any other suitable manner (e.g., after a certain period of time, etc.). The initial configuration view 204 may represent a day schedule view. The day schedule view can include a prompt that requests user input relating to which days the sleep alarm should go off. The user 130 may select which days by selecting one or more alarm selectors from a set of alarm selectors 224. The set of alarm selectors 224 may correspond to a week period, a shorter period, or a longer period.

The initial configuration view 206 may be presented in response to user input with the initial configuration view 204. For example, the user 130 may interact with the set of alarm selectors 224 to select one or more days on which the sleep alarm will go off. In response, the initial configuration view 206 may be presented. The initial configuration view 206 may represent an alarm time schedule view. The alarm time schedule view can include a prompt that requests user input relating to what time each day (selected using the initial configuration view 204) the sleep alarm should go off. The user 130 may select a time by interacting with a time selector 226.

The initial configuration view 208 may be presented in response to user input with the initial configuration view 206. For example, the user 130 may interact with the time selector 226. In response, the initial configuration view 208 may be presented. The initial configuration view 208 may represent a sleep duration view. The sleep duration view can include a prompt that requests user input relating a sleep duration corresponding to the sleep alarm. The user 130 may select a sleep duration by interacting with a sleep duration selector 228. Using the sleep duration and/or the alarm time, an appropriate time for a suggested bedtime may be determined.

The initial configuration view 210 may be presented in response to user input with the initial configuration view 208. For example, the user 130 may interact with the sleep duration selector 228. In response, the initial configuration view 210 may be presented. The initial configuration view 210 may represent a sleep alert view. The sleep alert view can include a prompt that requests user input relating to when to schedule a sleep alert. The sleep alert may be an alert, similar to an alarm alert, that goes off at an offset time prior to a suggested bedtime. For example, for a suggested bedtime of 10:00 pm, a sleep alert may be scheduled to go off at 9:30 pm (e.g., offset 30 minutes prior to the suggested bedtime). The user 130 may select a sleep alert offset time by interacting with a sleep reminder selector 230. Once the sleep alert offset time has been selected, the sleep alert may be scheduled.

The initial configuration view 212 may be presented in response to user input with the initial configuration view 210. For example, the user 130 may interact with the sleep reminder selector 230. In response, the initial configuration view 212 may be presented. The initial configuration view 212 may represent a sound selection view. The sound selection view may include one or more prompts that request user input relating to characteristics of how alerts associated with the sleep alarm and the sleep reminder will be presented. For example, the initial configuration view 212 may include a bedtime sound selector 232 and a wakeup sound selector 234. The bedtime sound selector 232 may correspond to the sleep reminder selected in the sleep reminder view (e.g., the initial configuration view 210). The wakeup sound selector 234 may correspond to the sleep alarm configured in the initial configuration views 204, 206. In some examples, instead of or in addition to sound, the selectors 232, 234 may enable selection of one or more other means for presenting alerts. For example, the other means may include changing a brightness on the screen of the user device 104 (or other user device), causing the user device 104 (or other user device) to vibrate, adjusting volume on the user device 104 (or other user device), adjusting elements in a sleeping environment (e.g., opening curtains, etc.), and the like.

The initial configuration view 214 may be presented in response to user input with the initial configuration view 212. For example, the user 130 may interact with the selectors 232, 234. In response, the initial configuration view 214 may be presented. The initial configuration view 214 may represent an informational view. The informational view may include information about the sleep alarm and, in particular, aspects of the adjustable sleep alarm indicator 122 and/or the sleep graph 124.

The initial configuration view 216 may be presented in response to user input with the initial configuration view 214. The initial configuration view 216 may represent the sleep alarm view 120. As described herein, the sleep alarm view 120 may include the adjustable sleep alarm indicator 122 and the sleep graph 124. The sleep alarm view 120 may also include a suggested bedtime indicator 236 and a wake time indicator 238. In some examples, each of the indicators 236, 238 may be selectable in order to adjust the suggested bedtime and the wake time, respectively. For example, the suggested bedtime indicator 236 may be selected by user input that identifies the "Bedtime" text, the graphical element, or the time "10:30 pm." Once selected, the time 10:30 pm can be adjusted by inputting an updated time or selecting an updated time from a list of times. The wake time indicator 238 may be selected and adjusted in a similar manner.

Figure 5:
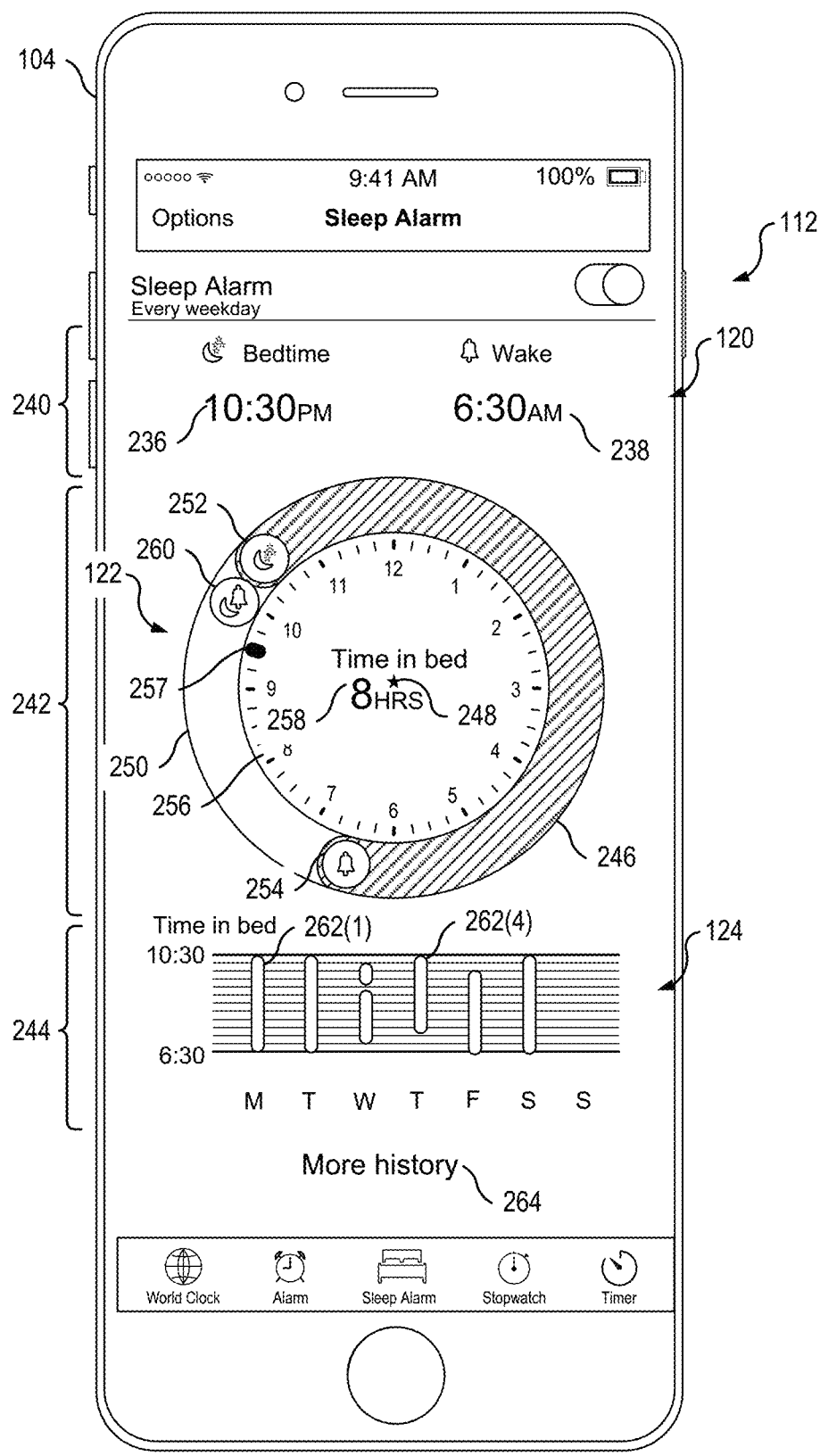
FIG. 5 illustrates an example sleep alarm view of an alarm graphical user interface on a user device for interacting with a sleep alarm as described herein, according to at least one example.

FIG. 5 illustrates the sleep alarm view 120 of the alarm graphical user interface 112 on the user device 104, according to at least one example. FIG. 5 may illustrate aspects of the sleep alarm view 120 in greater detail than previous figures described herein. The sleep alarm view 120 may be presented as part of a scheduling phase of an alarm setting sequence. In some examples, the sleep alarm view may be presented as part of a configuration phase of the alarm setting sequence. The sleep alarm view 120 may include the adjustable sleep alarm indicator 122, the sleep graph 124, the suggested bedtime indicator 236, and the wake time indicator 238. The suggested bedtime indicator 236 and the wake time indicator 238 may be disposed in a first region 240 of the sleep alarm view 120. The adjustable sleep alarm indicator 122 may be disposed in a second region 242 of the sleep alarm view 120. The sleep graph 124 may be disposed in a third region 244 of the sleep alarm view 120. In some examples, the sleep alarm view 120, as illustrated in FIG. 5 or otherwise, may be presented during a scheduling phase of an alarm setting sequence. In some examples, at least a portion of configuration information may be received via interaction with the sleep alarm view 120 of the alarm graphical user interface 112, as illustrated in FIG. 5.

The adjustable sleep alarm indicator 122 may include a variable graphical element 246 having a variable annular shape (e.g., ring shape). The variable graphical element 246 may be aligned relative to a center point 248 of the adjustable sleep alarm indicator 122. The variable graphical element 246 may be configured to move within a fixed annular range 250 relative to the center point 248 or other part of the adjustable sleep alarm indicator 122. Moving within the fixed annular range 250 may include the variable graphical element 246 increasing in size (e.g., increasing in length), decreasing in size (e.g., decreasing in length), rotating, and achieving any other suitable movement. The fixed annular range 250 may represent a bounded range in which the variable graphical element 246 moves.

The variable graphical element 246 may include an adjustable bedtime element 252 associated with a first end of the variable graphical element 246 and an adjustable wake time element 254 associated with a second end of the variable graphical element 246. In this manner, the elements 252, 254 may define the end points of the variable graphical element 246.

The adjustable bedtime element 252 may represent a first future time for a bedtime, which may correspond to the suggested bedtime indicator 236. For example, as illustrated in FIG. 5, the adjustable bedtime element 252 is aligned with 10:30 on a clock face 256 of the adjustable sleep alarm indicator 122 (e.g., the suggested bedtime indicator 236 also identifies 10:30). Thus, the first future time corresponding to the suggested bedtime may be computed based at least in part on configuration information relating to a sleep duration 258 and a second future time corresponding to a wake time (e.g., as represented by the wake time indicator 238). In some examples, the suggested bedtime may be input by the user 130 interacting with the suggested bedtime indicator 236. The adjustable sleep alarm indicator 122 may also include a current time indicator 257. The current time indicator 257 may function to indicate a current time (e.g., 9:30).

As described in detail herein, the adjustable bedtime element 252 may be moveable within the fixed annular range 250 independent of the adjustable wake time element 254. For example, movement of the adjustable bedtime element 252 within the fixed annular range 250 may cause the variable graphical element 246 to increase in size and decrease in size, with the adjustable wake time element 254 remaining at the same location. Such movement of the adjustable bedtime element 252 may cause the first future time corresponding to the suggested bedtime to update based at least in part on the location of the adjustable bedtime element 252 within the fixed annular range 250. Such movement of the adjustable bedtime element 252 may also cause the sleep duration 258 to update based at least in part on the location of the adjustable bedtime element 252 within the fixed annular range 250.

The adjustable wake time element 254 may represent the second future time for presenting a wakeup alert, which may correspond to the wake time indicator 238. For example, as illustrated in FIG. 5, the adjustable wake time element 254 is aligned with 6:30 on the clock face 256 of the adjustable sleep alarm indicator 122 (e.g., the wake time indicator 238 also identifies 6:30). The second future time may be computed based at least in part on configuration information received previously. In some examples, the second future time for presenting the wakeup alert may be input by the user 130 by interacting with the wake time indicator 238 and/or the adjustable sleep alarm indicator 122.

As described in detail herein, the adjustable wake time element 254 may be dependently moveable within the fixed annular range 250. For example, movement of the adjustable wake time element 254 within the fixed annular range 250 a first amount may cause the adjustable bedtime element 252 to also move the first amount. In this example, the size (e.g., length) of the variable graphical element 246 may remain the same, with the adjustable wake time element 254 and the adjustable bedtime element 252 moving dependently. Such movement of the adjustable wake time element 254 may cause the first future time corresponding to the suggested bedtime to update based at least in part on the location of the adjustable bedtime element 252 within the fixed annular range 250. Such movement of the adjustable wake time element 254 may also cause the second future time corresponding to the wake time to update based at least in part on the location of the adjustable wake time element 254 within the fixed annular range 250.

The adjustable sleep alarm indicator 122 may also include a variable alert element 260. The variable alert element 260 may be moveable within the fixed annular range 250 to any suitable location within the fixed annular range 250. For example, the user 130 may select the variable alert element 260 and slide it within the fixed annular range 250. In this manner the variable alert element 260 may rotate about the center point 248. In some examples, the variable alert element 260 may correspond to a scheduled time for a sleep alert or any other suitable alert. In a sleep alert example, the variable alert element 260 may be located at a time that corresponds to a time earlier than the adjustable bedtime element 252. For example, as illustrated in FIG. 5, the variable alert element 260 is disposed at a location in the fixed annular range 250 that corresponds to 10:00 on the clock face 256. This may mean that the sleep alert is scheduled to go off at 10:00 (e.g., 30 minutes prior to the suggested bedtime of 10:30). In some examples, the location of the variable alert element 260 with respect to the fixed annular range 250 may dictate a scheduled time for the alert. Other suitable alerts include, for example, alerts scheduled after the suggested bedtime (e.g., an alert scheduled for 2:00 am to feed a newborn baby or let a dog out), alerts scheduled after the wake time (e.g., an alert scheduled for 7:00 am as a backup alarm to the sleep alarm scheduled for 6:30 am). In some examples, more than one variable alert element 260 may be provided as part of the adjustable sleep alarm indicator 122. In this manner, more than one alert may be scheduled using the adjustable sleep alarm indicator 122. In some examples, the graphical representation of the sleep alarm element(s) 260 with respect to the clock face 256 may be beneficial for users of the sleep alarm to understand aspects of their sleep routines. In some examples, instead of variable alert element 260 may simply represent a sleep alert and may be a tick mark or other indicator on the clock face 256. The tick mark may graphically represent the scheduled time for the sleep alert, but may not allow the user 130 to adjust the scheduled time. For example, the scheduled time may be set during the configuration phase of the alarm setting sequence and may persist for future alarms.

The sleep graph 124 may include one or more linear graphical indicators 262(1)-262(n). A few of the linear graphical indicators 262(1), 262(4) are identified in the sleep graph 124 of FIG. 5. Each linear graphical indicator 262 may correspond to an interval of time such as a 12-hour interval (e.g., 6 pm on day 1 to 6 am on day 2), a 24-hour interval (6 pm on day 1 to 6 pm on day 2), a typical day (e.g., 12 am on day 1 to 12 am on day 2), a night interval (e.g., 6 pm on day 1 to 9 am on day 2), and any other suitable interval. The number of intervals (e.g., the number of linear graphical indicators 262) displayed in the sleep graph 124 may correspond to any suitable period (e.g., a week, a month, etc.). In the sleep graph 124, each of the linear graphical indicators 262 may correspond to a day interval of a calendar week period (e.g., Monday through Sunday). As described in detail herein, the sleep graph 124 may represent sleep patterns of the user 130 who uses the sleep alarm. In this manner, the sleep graph 124 may be generated based at least in part on historical sleep data. Selection of a more history selector 264, may cause presentation of additional historical sleep data for other periods (e.g., earlier weeks, months, years, etc.).

Figure 6:
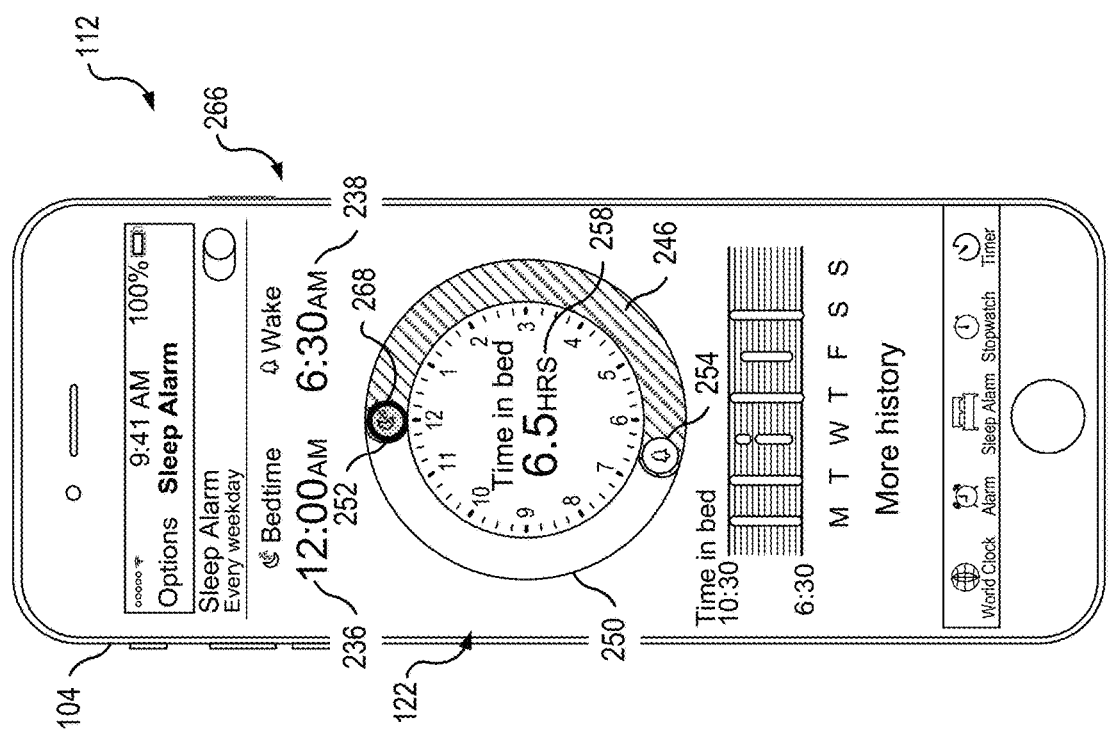
FIG. 6 illustrates example sleep alarm views of an alarm graphical user interface on a user device for interacting with a sleep alarm as described herein, according to at least one example.
Figure 6:
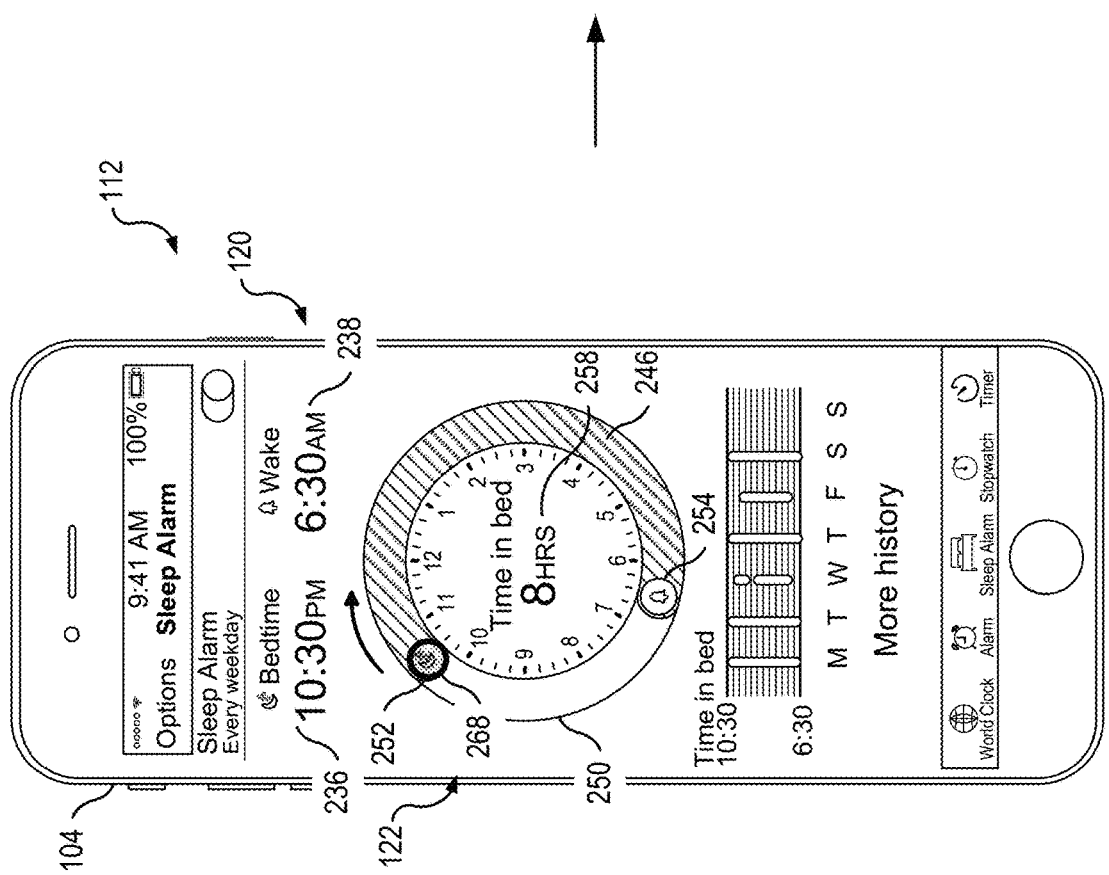

FIG. 6 illustrates the sleep alarm view 120 and an updated sleep alarm view 266 of the alarm graphical user interface 112 on the user device 104, according to at least one example. The updated sleep alarm view 266 may be considered an updated version of the sleep alarm view 120. This may be because certain aspects of the alarm graphical user interface 112 have been adjusted between the state illustrated as the sleep alarm view 120 and the state illustrated as the updated sleep alarm view 266.

In some examples, the sleep alarm view 120 may represent a first state of the alarm graphical user interface 112 prior to receiving a user input 268 at the user device 104 (e.g., at an input component such as a touch screen). The user input 268 (and other user inputs described herein) may be depicted as a dark circular element with a dimpled hatching. The updated sleep alarm view 266 may represent a second state of the alarm graphical user interface 112 after receiving the user input 268. The user input 268 is illustrated as a touch gesture that contacts the adjustable bedtime element 252 and moves the adjustable bedtime element 252 to the right (e.g., clockwise) in FIG. 6. The user input 268 at the adjustable bedtime element 252 may move the adjustable bedtime element 252 in a clockwise direction without also moving the adjustable wake time element 254. In this manner, the adjustable bedtime element 252 may move independent of the adjustable wake time element 254. Thus, the adjustable wake time element 254 remains in the same location in both views 120, 266. At the same time, the adjustable bedtime element 252 has changed locations between views 120, 266.

Because one end of the variable graphical element 246 has moved (e.g., the adjustable bedtime element 252), the length of the variable graphical element 246 has also changed. In the example illustrated in FIG. 6, the length of the variable graphical element 246 is shorter in the updated sleep alarm view 266 as compared to the sleep alarm view 120. The suggested bedtime indicator 236 is also updated to reflect an updated future time for the suggested bedtime (e.g., 10:30 pm in the sleep alarm view 120 and 12:00 am in the updated sleep alarm view 266). The wake time indicator 238 remains unchanged between the two views 120, 266. This may be because the adjustable wake time element 254 has not moved. The sleep duration 258 is updated to reflect the change to the location of the adjustable bedtime element 252 in the updated sleep alarm view 266. In some examples, the sleep duration 258 may correspond directly to the length of the variable graphical element 246. For example, if the adjustable bedtime element 252 were moved to the left (e.g., counter-clockwise), the length of the variable graphical element 246 would increase (e.g., get longer), the sleep duration 258 would increase, and the suggested bedtime indicator 236 would change.

Figure 7:
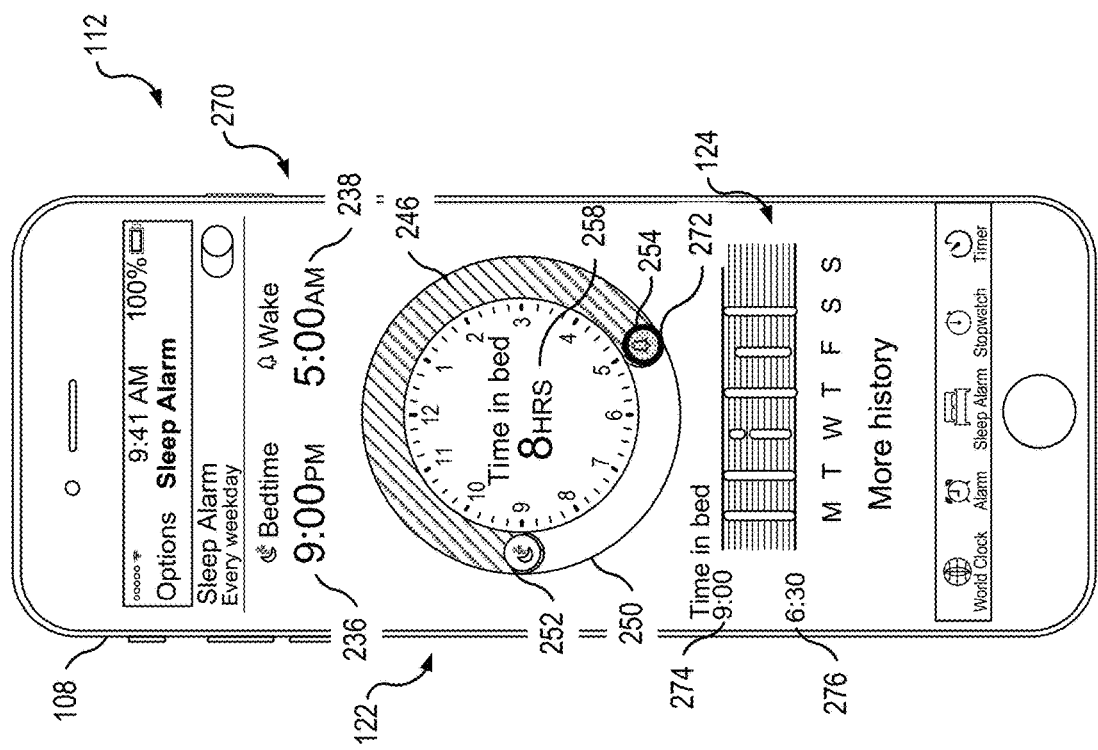
FIG. 7 illustrates example sleep alarm views of an alarm graphical user interface on a user device for interacting with a sleep alarm as described herein, according to at least one example.
Figure 7:
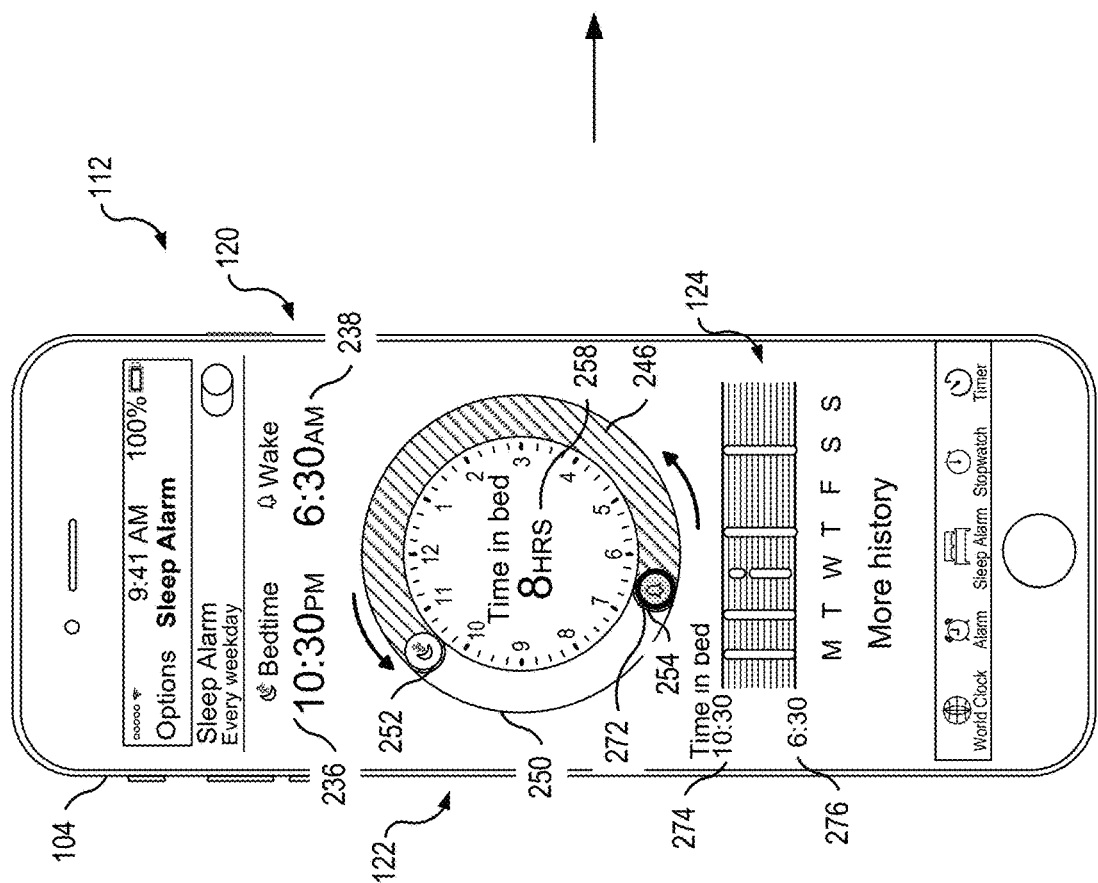

FIG. 7 illustrates the sleep alarm view 120 and an updated sleep alarm view 270 of the alarm graphical user interface 112 on the user device 104, according to at least one example. The updated sleep alarm view 270 may be considered an updated version of the sleep alarm view 120. This may be because certain aspects of the alarm graphical user interface 112 have been adjusted between the state illustrated as the sleep alarm view 120 and the state illustrated as the updated sleep alarm view 270.

In some examples, the sleep alarm view 120 may represent a first state of the alarm graphical user interface 112 prior to receiving a user input 272 at the user device 104 (e.g., at an input component such as a touch screen). The updated sleep alarm view 270 may represent a second state of the alarm graphical user interface 112 after receiving the user input 272. The user input 272 is illustrated as a touch gesture that contacts the adjustable wake time element 254 and moves the adjustable wake time element 254 to the right in FIG. 7 (e.g., counter-clockwise). The user input 272 at the adjustable wake time element 254 may cause the variable graphical element 246, including both the adjustable bedtime element 252 and the adjustable wake time element 254, to rotate in a counter-clockwise direction within the fixed annular range 250. In particular, the single user input 272 may cause the adjustable wake time element 254 and the adjustable bedtime element 252 to both move within the fixed annular range 250. Thus, as shown in FIG. 7, both the adjustable wake time element 254 and the adjustable bedtime element 252 have changed locations between the views 120, 270.

Because both ends of the variable graphical element 246 have moved (e.g., the adjustable bedtime element 252 and the adjustable wake time element 254) similar distances, the length of the variable graphical element 246 has remained unchanged. For the same reasons, the suggested bedtime indicator 236 is updated to reflect an updated first future time for the suggested bedtime (e.g., 10:30 pm in the sleep alarm view 120 and 9:00 pm in the updated sleep alarm view 270) and the wake time indicator 238 is updated to reflect a second updated future time for the wakeup alert (e.g., 6:30 am in the sleep alarm view 120 and 5:00 am in the updated sleep alarm view 270). The sleep duration 258 remains unchanged between the two views 120, 270. This is at least because the length of the variable graphical element 246 has remained constant while the ends have moved.

The sleep graph 124 may also be updated based at least in part on one or more of the updated locations (and times) of the adjustable bedtime element 252 and the adjustable wake time element 254 in the updated sleep alarm view 270. For example, the sleep graph 124 may include an earliest bedtime 274 and a latest wake time 276. The earliest bedtime 274 may correspond to an earliest time recorded during the period presented in the sleep graph 124 (e.g., a week) as an actual bedtime or a suggested bedtime. The latest wake time 276 may correspond a latest time recording during the period in the sleep graph 124 (e.g., a week) as an actual wake time or a time associated with a sleep alert. Thus, in the sleep alarm view 120 the earliest bedtime 274 was 10:30 pm and the latest wake time 276 was 6:30 am. In the updated sleep alarm view 270, the suggested bedtime (e.g., as shown in the suggested bedtime indicator 236) has changed to 9:00 pm. Because 9:00 pm is earlier than 10:30 pm, the earliest bedtime 274 has been updated in the updated sleep alarm view 270 to reflect 9:00 pm. The latest wake time 276, however, has not been changed between the views 120, 270. This may be because the wake time of 6:30 am (e.g., as shown in the wake time indicator 238 as a time for a wakeup alert) in the sleep alarm view 120 is later than the wake time of 5:00 am (e.g., as shown in the wake time indicator 238 as a time for a wakeup alert) in the updated sleep alarm view 270.

Figure 8:
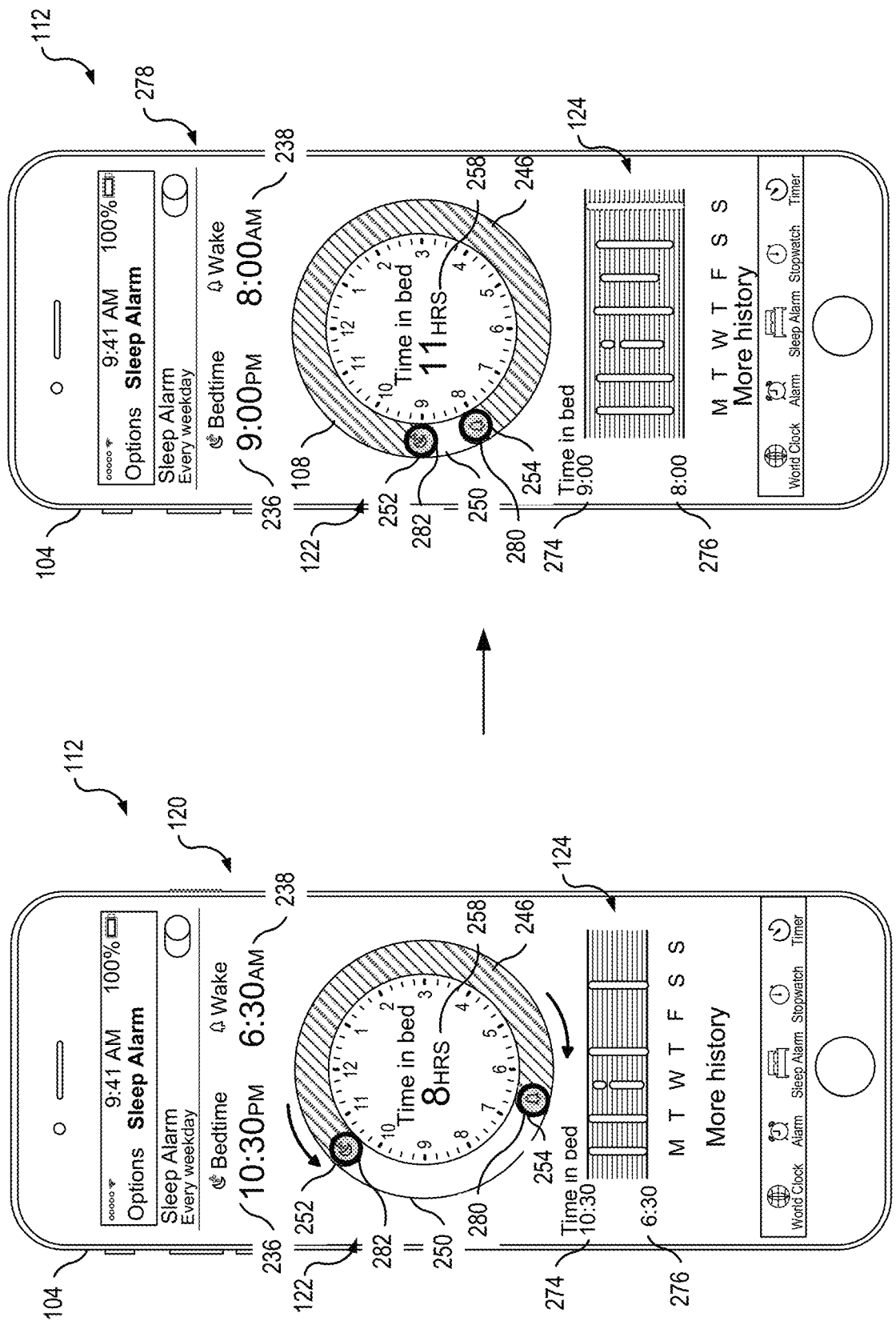
FIG. 8 illustrates example sleep alarm views of an alarm graphical user interface on a user device for interacting with a sleep alarm as described herein, according to at least one example.

FIG. 8 illustrates the sleep alarm view 120 and an updated sleep alarm view 278 of the alarm graphical user interface 112 on the user device 104, according to at least one example. The updated sleep alarm view 278 may be considered an updated version of the sleep alarm view 120. This may be because certain aspects of the alarm graphical user interface 112 have been adjusted between the state illustrated as the sleep alarm view 120 and the state illustrated as the updated sleep alarm view 278.

In some examples, the sleep alarm view 120 may represent a first state of the alarm graphical user interface 112 prior to receiving user inputs 280, 282 at the user device 104 (e.g., at an input component such as a touch screen). The updated sleep alarm view 278 may represent a second state of the alarm graphical user interface 112 after receiving the user inputs 280, 282. The user input 280 is illustrated as a touch gesture that contacts the adjustable wake time element 254 and moves the adjustable wake time element 254 to the left in FIG. 8 (e.g., clockwise) from 6:30 am to 8:00 am. The user input 280 at the adjustable wake time element 254 may cause the variable graphical element 246, including both the adjustable bedtime element 252 and the adjustable wake time element 254, to rotate in a clockwise direction within the fixed annular range 250. The user input 282 is illustrated as a touch gesture that contacts the adjustable bedtime element 252 and moves bedtime element 252 to the left in FIG. 8 (e.g., counter-clockwise). The user input 282 at the adjustable bedtime element 252 may cause the adjustable bedtime element 252 to move in a counter-clockwise direction the fixed annular range 250 independent of the adjustable wake time element 254.

In the updated sleep alarm view 278, because both ends of the variable graphical element 246 have moved (e.g., the adjustable bedtime element 252 and the adjustable wake time element 254), the length of the variable graphical element 246 has increased. For the same reasons, the suggested bedtime indicator 236 is updated to reflect an updated first future time for the suggested bedtime (e.g., 10:30 pm in the sleep alarm view 120 and 9:00 pm in the updated sleep alarm view 270) and the wake time indicator 238 is updated to reflect a second updated future time for the wakeup alert (e.g., 6:30 am in the sleep alarm view 120 and 8:00 am in the updated sleep alarm view 278). The sleep duration 258 is also updated in the updated sleep alarm view 278 (e.g., 8 hours in the sleep alarm view 120 and 11 hours in the updated sleep alarm view 278). This is at least because the length of the variable graphical element 246 has increased within the fixed annular range 250.

The sleep graph 124 may also be updated based at least in part on one or more of the updated locations (and times) of the adjustable bedtime element 252 and the adjustable wake time element 254 in the updated sleep alarm view 278. In the sleep alarm view 120, the earliest bedtime 274 was 10:30 pm and the latest wake time 276 was 6:30 am. In the updated sleep alarm view 278, the suggested bedtime (e.g., as shown in the suggested bedtime indicator 236) has changed to 9:00 pm. Because 9:00 pm is earlier than 10:30 pm, the earliest bedtime 274 has been updated in the updated sleep alarm view 278 to reflect 9:00 pm. In the updated sleep alarm view 278, the future time for the wakeup alert (e.g., as shown in the wake time indicator 238) has changed to 8:00 am. Because 8:00 am is later than 6:30 am, the earliest bedtime 274 has been updated in the updated sleep alarm view 278 to reflect 8:00 am. As described in detail herein, other aspects of the sleep graph 124 (e.g., the scale, the range, etc.) may be updated based at least in part on the earliest bedtime 274 and the latest wake time 276.

Figure 9:
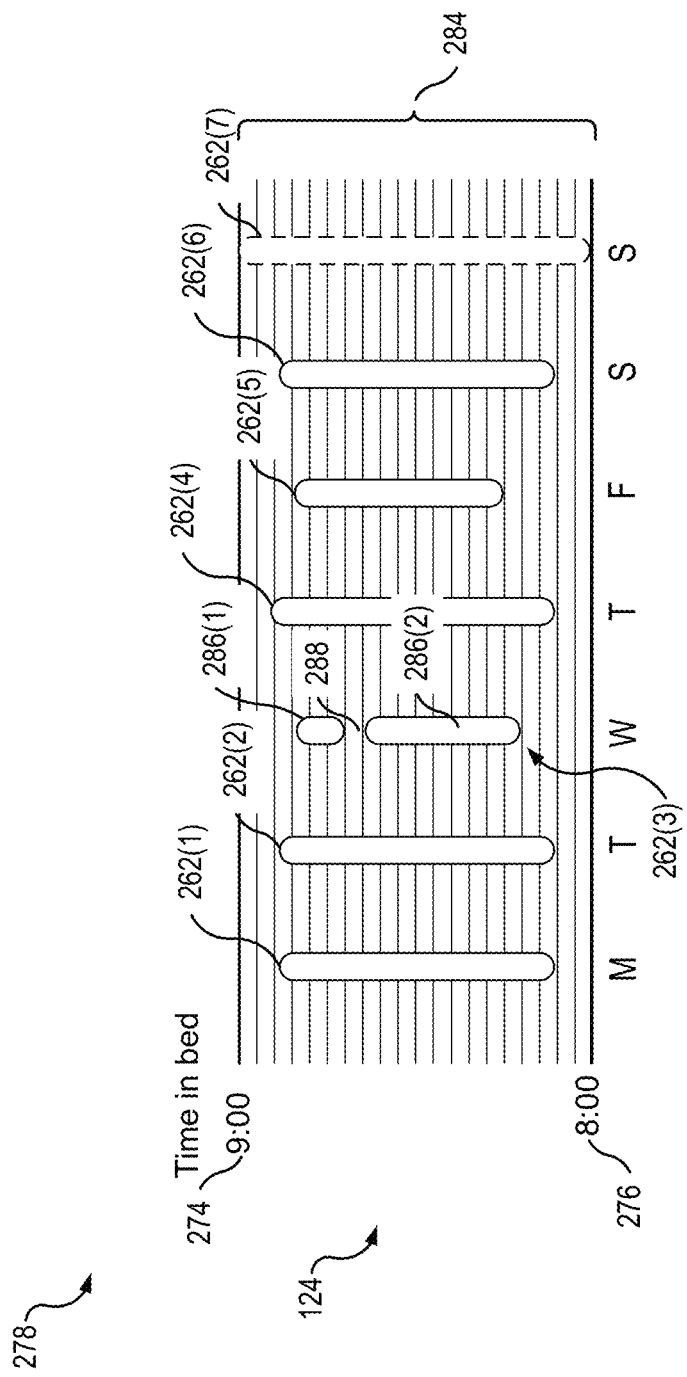
FIG. 9 illustrates an example sleep graph of a sleep alarm view of an alarm graphical user interface for interacting with a sleep alarm as described herein, according to at least one example.

FIG. 9 illustrates the sleep graph 124 of the updated sleep alarm view 278 of the alarm graphical user interface 112 on the user device 104, according to at least one example. As introduced herein, the sleep graph 124 may include the linear graphical indicators 262(1)-262(n). A few of the linear graphical indicators 262(1)-262(7) are identified in the sleep graph 124. Each linear graphical indicator 262 may correspond to an interval of time such as a 12-hour interval (e.g., 6 pm on day 1 to 6 am on day 2), a 24-hour interval (6 pm on day 1 to 6 pm on day 2), a typical day (e.g., 12 am on day 1 to 12 am on day 2), a night interval (e.g., 6 pm on day 1 to 9 am on day 2), and any other suitable interval. The number of intervals (e.g., the number of linear graphical indicators 262) displayed in the sleep graph 124 may correspond to any suitable period (e.g., a week, a month, etc.). In the sleep graph 124, each of the linear graphical indicators 262 may correspond to a day interval of a calendar week period (e.g., Monday through Sunday).

The linear graphical indicators 262 may be graphed on the sleep graph 124 with respect to a sleep range 284. The sleep range 284 may correspond to the earliest bedtime 274 and the latest wake time 276 for the period (e.g., a week). The sleep range 284 may be varied depending on how the adjustable sleep alarm indicator 122 (and the sleep alarm) is configured. This includes updating the sleep range 284 based at least in part on a suggested bedtime to take place in the future and a wake time to take place in the future. In this manner, the user 130 may be able to see how adjusting her sleep for a single night relates to other earlier nights of sleep during the week. For example, as discussed with reference to FIG. 8, the suggested bedtime and the wake time were adjusted between the sleep alarm view 120 and the updated sleep alarm view 278, which resulted in the sleep range 284 illustrated in FIG. 9. In some examples, the linear graphical indicator 262(7) may be an expected linear graphical indicator. This may be because the sleep graph 124 illustrated in FIG. 9 corresponds to a time Sunday after 7:00 am (the time the user 130 awoke on Sunday morning as indicated by the linear graphical indicator 262(6)) and before 9:00 pm (the time currently scheduled as a suggested bedtime on Sunday night for the user 130 as indicated by the linear graphical indicator 262(7)). Thus, the linear graphical indicator 262(7) corresponds to expected sleep during Sunday night. As discussed with reference to FIG. 8, the sleep duration 258 for the updated sleep alarm view 278 was 11 hours. Thus, the linear graphical indicator 262(7) extends from 9:00 pm to 8:00 am.

Generally, each of the linear graphical indicators 262 may represent an amount of sleep recorded and/or estimated during an interval, a beginning of the sleep interval, and an end of the sleep interval. The amount of sleep may correspond to the length of the linear graphical indicator 262. The beginning of the sleep interval may correspond to a first end of the linear graphical indicator 262 and the end of the sleep interval may correspond a second end of the linear graphical indicator 262. When the linear graphical indicator 262 includes more than two ends (e.g., the linear graphical indicator 262(3)), the beginning of the sleep interval may correspond to the earliest end and the end of the sleep interval may correspond to the latest end of the linear graphical indicator 262. Thus, the linear graphical indicators 262 may represent a total amount of sleep the user 130 received each night and an aggregate total for the week. Because adequate sleep may impact one's health, the presentation of the linear graphical indicators 262 in a manner that represents amount of sleep may enable the user 130 to determine whether to make changes in her sleep routine to increase or decrease the amount of time slept.

The linear graphical indicators 262 may also represent instances of sleep interruptions. For example, the linear graphical indicator 262(3) may include graphical segments 286(1), 286(2) separated by a broken region 288. The graphical segment 286(1) may represent that the user 130 slept for a first period of time (e.g., around 1.5 hours). The broken region 288 may represent that after the first period of time corresponding to the graphical segment 286(1), the user 130 was awake for a second period of time (e.g., around half an hour). The graphical segment 286(2) may represent that after the second period of time corresponding to the broken region 288, the user 130 slept for a third period of time (e.g., around 4.5 hours). Thus, the linear graphical indicator 266(3) can be used to easily see that for Wednesday night the user 130 slept around 6 hours total, with a short interruption of about 30 minutes. In some example, more or fewer graphical segments 286 and broken regions 288 may be included in any one of the linear graphical indicator 262, depending on sleep data. Thus, the linear graphical indicators 262 may represent instances of sleep interruptions during each night and display all instances of interruptions during a certain period (e.g., a week). Because uninterrupted sleep may impact one's health, the presentation of the linear graphical indicators 262 in a manner that represents instances of sleep interruptions may enable the user 130 to determine whether to make changes in her sleep routine to eliminate or minimize the number, frequency, and length of interruptions.

Each of the linear graphical indicators 262 or a set of linear graphical indicators 262 together, when graphed with respect to the sleep range 284, may represent how consistent the user 130 is in her sleep routine in terms of alignment of the linear graphical indicators 262. For example, if the linear graphical indicators 262 include the same beginning time and end time (e.g., are aligned), it may be said that the user's 130 sleep routine has characteristics of consistency. Thus, consistency may refer to instances of retiring and rising at similar times each day. Because consistency in one's sleep routine may impact one's health, the presentation of the linear graphical indicators 262 in a manner that represents consistency may enable the user 130 to determine whether to make changes in her sleep routine to improve consistency.

The retiring times and rising times may correspond to the beginnings of the sleep intervals and the ends of the sleep intervals, as described herein. Thus, for a particular interval, the times for retiring and rising may correspond to a suggested bedtime (e.g., a computed value indicating a time to go to sleep) and a wake time (e.g., a computed and/or scheduled value indicating a time when a wakeup alert of the sleep alarm will go off) for that interval. Thus, the determination of the beginning of the sleep interval and the end of the sleep interval may be based at least in part on system data, interaction data, and/or configuration information relating times computed and/or scheduled for the suggested bedtimes and the wake times.

In some examples, as discussed with reference to FIG. 10, determination of the beginning of the sleep interval and the end of the sleep interval may be based at least in part on user interaction data collected from the user device 104, other electronic devices associated with the user 130 of the user device 104, and/or other devices capable of transmitting information over a network.

Figure 10:
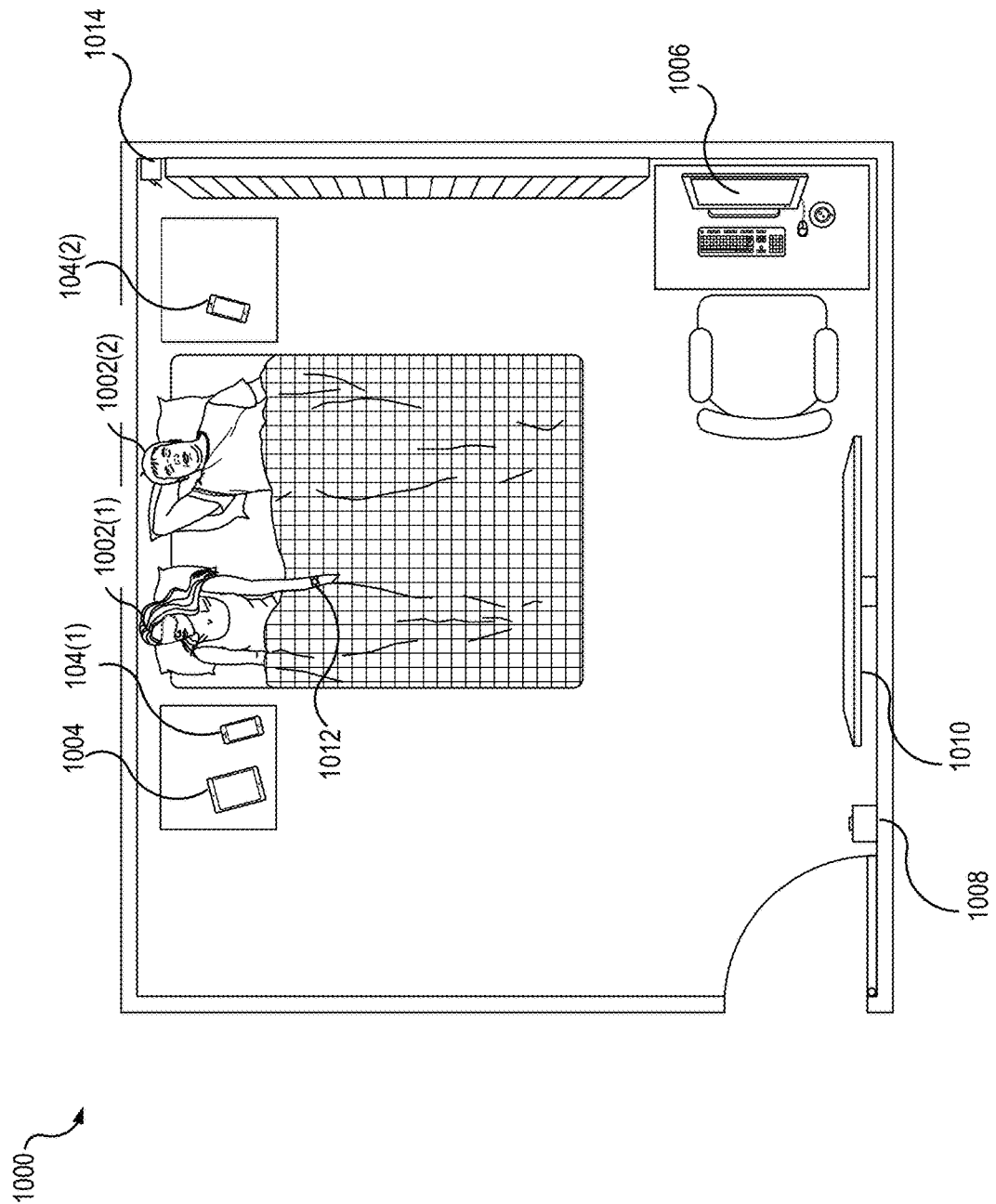
FIG. 10 illustrates an example environment in which techniques relating to interacting with a sleep alarm as described herein may be implemented, according to at least one example.

FIG. 10 illustrates an example environment 1000 in which techniques relating to interacting with a sleep alarm as described herein may be implemented, according to at least one example. In particular, the environment 1000 may be useful for collecting historical sleep data in order to populate the sleep graph 124. This may include determining and/or estimating when a user falls asleep (e.g., a beginning of a sleep interval), determining and/or estimating when the user is awake during the night (e.g., instances of sleep interruptions during the sleep interval), and/or determining and/or estimating when the user wakes in the morning (e.g., an end of the sleep interval). This sleep data may collected in any suitable manner, shared with any suitable user device (e.g., the user device 104), and/or shared with a service provider computer (e.g. a service provider 1102) to populate the sleep graph 124.

The environment 1000 may be any suitable location where users 1002(1)-1002(n) are located and sleep. The users 1002 are examples of the user 130. The environment 1000 may be a room in a home, a studio apartment, a hotel room, a cabin on a train or airplane, a classroom, and any other suitable location. The environment 1000 may include a plurality of network-enabled devices such as user devices 104(1), 104(2), a tablet device 1004, a desktop computer or a laptop computer 1006, a smart outlet 1008, a home entertainment device and/or smart TV 1010, a wearable device 1012, an automated blind controller 1014, and any other suitable device (e.g., an alarm system that includes light sensors, door sensors, window sensors, etc.). The devices of the environment 1000 may provide data to the user device 104 and/or the service provider that can be used to determine or estimate when the users 1002 fall asleep, instances when the users 1002 are awake during the night, and when the users 1002 wake up in the morning. Such data can include interaction data indicating that one of the users 1002 is interacting with a device, lock data indicating that a device has been put in a locked state or hibernation state, power status data, and any other suitable data.

For example, if the user 1002(1) were playing a game on the tablet device 1004, interaction data from the tablet device 1004 may identify the user 1002(1) (e.g., by using login information or other user profile information associated with the user 1002(1)), the tablet device 1004, a time when the interactions were logged, the type of interaction (e.g., playing the game using an application, viewing device, interacting with email, checking a social media site, viewing video content, etc.), and any other suitable data.

As an additional example, if the user 1002(2) awakes during the night, he may check the time on his user device 104(2). This event may be logged by interaction data that identifies the user 1002(2), the user device 104(2), the duration of the event (e.g., how long was the user device 104(2) unlocked, how long was the screen lit up, or how long was the clock application open), the type of interaction, and any other suitable data.

As an additional example, if the home entertainment device 1010 is on and receiving content, it may be inferred that at least one of the users 1002 is awake. If it is determined that only the user device 104(2) is located in the environment 1000 at the time when the home entertainment device 1010 is on, it may be inferred that at least the user 1002(2) is awake.

As an additional example, the wearable device 1012, which may include one or more sensors, may be capable of collecting movement data that identifies when the user 1002(1) is moving and/or health data that identifies aspects of her heart rate, respiratory rate, etc. This data may be used to determine that the user 1002(1) is asleep and/or awake.

As an additional example, the smart outlet 1008 may provide data indicating that the smart outlet 1008 is providing power to a connected device (e.g., a lamp, light fixture, etc.). This data may be used to determine that the users 1002 are asleep and/or awake. Similarly, the automated blind controller 1014 may provide data indicating that a set of blinds are open. This data may be used to determine that the users 1002 are asleep and/or awake.

In some examples, the environment 1000 may include other devices, which may or may not be network-enabled. For example, a sleep monitoring device may collect detailed sleep data about the user 1002(1). This data may be shared with the user device 104 and/or the service provider in any suitable fashion in order to implement techniques described herein. In some examples, certain third-party applications running on the user devices 104 and/or the tablet device 1004 may be used to collect sleep data that may be used to implement techniques described herein. For example, a particular sleep application may instruct the user 1002(1) to place the user device 104(1) on the bed next to her. The sleep application may use sensors of the user device 104(1) to collect data about movements of the user 1002(1) during the night. This movement data may then be used to determine when the user 1002(1) is asleep (including instances of Rapid Eye Movement (REM) sleep and non-REM sleep), is awake during the night, and is awake in the morning.

In some examples, the environment 1000 may also be useful for presenting one or more alerts as described herein (e.g., sleep alerts, wakeup alerts, and any other suitable alert). For example, the alerts may be presented as audio alerts at one or more of the devices that include speakers or other audio output devices (e.g., the user devices 104, the tablet device 1004, the desktop computer 1006, the home entertainment device 1010, and/or the wearable device 1012).

The alerts may be also presented as visual alerts at one or more of the devices. For example, displays or light elements of one or more of the user devices 104, the tablet device 1004, the desktop computer 1006, the home entertainment device 1010, and/or the wearable device 1012 may be turned on, flashed, brightness changed, or any other change to provide visual alerts. Visual alerts may also be presented by the smart outlet 1008 turning on a connected light, causing a brightness of the connected light to increase, flashing the connected light, or any other change to provide visual alerts. Visual alerts may also be presented by the automated blind controller 1014 opening a set of associated blinds and allowing natural light into the room. Any of the visual alerts may be presented in a manner that simulates a sunrise or otherwise slowly increases in brightness.

The alerts may also be presented as vibratory alerts at one or more of the devices. For example, vibration motors of the user devices 104, the tablet device 1004, and/or the wearable device 1012 may be turned on to provide the vibratory alerts.

In some examples, any suitable combination of audio, visual, and/or vibratory alerts may be presented at the same time as part of the same sleep alert, wakeup alert, or other comparable alert. For example, if the user 1002(1) is working at the desktop computer 1006 at a scheduled time for a sleep alert, it may be determined to send the sleep alert to the desktop computer 1006 as an audio alert and/or a visual alert (e.g., a popup on the screen of the desktop computer). The same sleep alert may also be sent to the wearable device 1012 if it is determined that the user 1002(1) is wearing the wearable device 1012. As an additional example, a wakeup alert may be presented as an audio alert at the user device 104(1), a visual alert by the automated blind controller 1014 opening the blinds, and as a vibratory alert at the wearable device 1012.

In some examples, interaction data may be collected that describes the interactions of the users 1002 with the devices (and other devices) in the environment 1000. This interaction data may be used in addition to or instead of certain configuration information typically received by user input. For example, instead of using the sleep duration selector 228 to select an offset time prior to a suggested bedtime for presentation of a sleep alert, the interaction data may be used to determine an estimated offset time. For example, historical interaction data may be used to model the behaviors of the user 1002(1) in the hours and minutes prior to the user 1002(1) falling asleep or at least getting in bed. Use of the historical interaction data may enable detection of one or more patterns of interaction with devices that may correspond to a sleep routine. For example, it may be determined that the user 1002(1) is typically in bed within 20 minutes after powering off an entertainment device in a family room. And that during this 20 minutes, the user 1002(1) turns on and off lights in the bathroom, opens and closes a door to a child's bedroom, turns down the thermostat, and interacts with her user device 104(1) before retiring. Based at least in part on this interaction data, it may be determined that the sleep alert should be sent to the user at least 20 minutes prior to the suggested bedtime. This may ensure that the user 1002(1) has sufficient time to conduct her bedtime routine prior to getting in bed. The determined time for the sleep alert may be customized to each of the users 1002(1), 1002(2). For example, the user 1002(2) may take much longer to go through his bedtime routine (as determined based at least in part on interaction data). Thus, a sleep alert may be sent to the user 1002(2) 30 minutes or more before his suggested bedtime.

Figure 11:
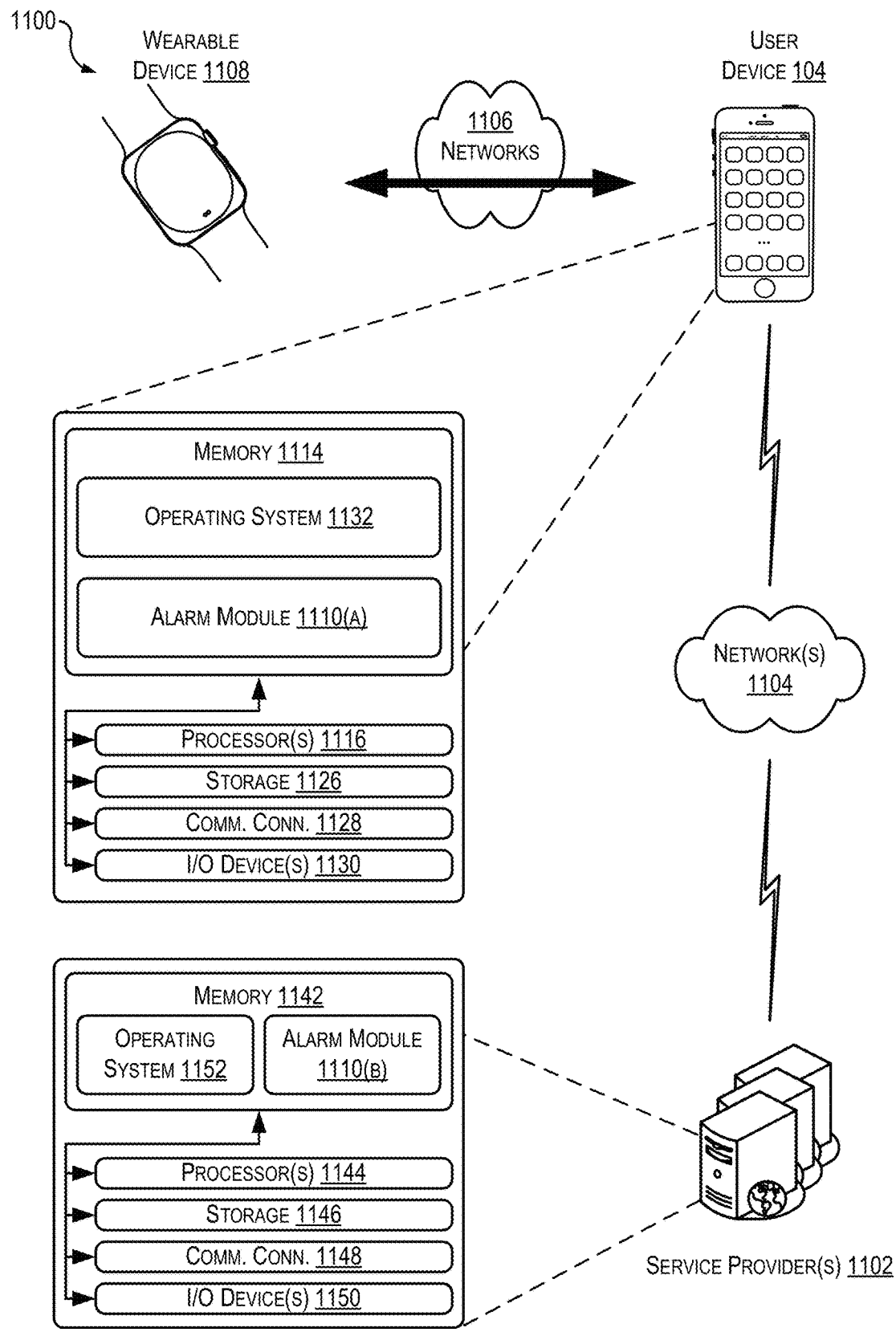
FIG. 11 illustrates a simplified block diagram including an example architecture for interacting with a sleep alarm as described herein, according to at least one example.

FIG. 11 illustrates an example architecture or environment 1100 configured to implement techniques relating to interacting with sleep alarms, according to at least one example. In some examples, the example architecture 1100 may further be configured enable the user device 104, service provider computers 1102, and a wearable device 1108 to share information. In some examples, the devices may be connected via one or more networks 1104 and/or 1106 (e.g., via Bluetooth, WiFi, the Internet, or the like). In the architecture 1100, one or more users (e.g., the user 130) may utilize the user device 104 to manage, control, or otherwise utilize the wearable device 1108, via the one or more networks 1106. Additionally, in some examples, the wearable device 1108, the service provider computers 1102, and user device 104 may be configured or otherwise built as a single device. For example, the wearable device 1108 and/or the user device 104 may be configured to implement the embodiments described herein as a single computing unit, exercising the examples described above and below without the need for the other devices described.

In some examples, the networks 1104, 1106 may include any one or a combination of many different types of networks, such as cable networks, the Internet, wireless networks, cellular networks, satellite networks, other private and/or public networks, or any combination thereof. While the illustrated example represents the user device 104 accessing the service provider computers 1102 via the networks 1104, the described techniques may equally apply in instances where the user device 104 interacts with the service provider computers 1102 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 104 may be configured to collect and/or manage user activity data potentially received from the wearable device 1108. In some examples, the wearable device 1108 may be configured to provide health, fitness, activity, and/or medical data of the user to a third- or first-party application (e.g., the service provider 1102). In turn, this data may be used by the user device 104 to schedule and present alerts as described herein. The user device 104 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 104 may be in communication with the service provider computers 1102 and/or the wearable device 1108 via the networks 1104, 1106, or via other network connections.

In one illustrative configuration, the user device 104 may include at least one memory 1114 and one or more processing units (or processor(s)) 1116. The processor(s) 1116 may be implemented as appropriate in hardware, computer-executable instructions, firmware, or combinations thereof. Computer-executable instruction or firmware implementations of the processor(s) 1116 may include computer-executable or machine-executable instructions written in any suitable programming language to perform the various functions described. The user device 104 may also include geo-location devices (e.g., a global positioning system (GPS) device or the like) for providing and/or recording geographic location information associated with the user device 104.

The memory 1114 may store program instructions that are loadable and executable on the processor(s) 1116, as well as data generated during the execution of these programs. Depending on the configuration and type of the user device 104, the memory 1114 may be volatile (such as random access memory (RAM)) and/or non-volatile (such as read-only memory (ROM), flash memory, etc.). The user device 104 may also include additional removable storage and/or non-removable storage 1126 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1114 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 1114 and the additional storage 1126, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 1114 and the additional storage 1126 are both examples of non-transitory computer storage media. Additional types of computer storage media that may be present in the user device 104 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 104. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 104 may also contain communications connection(s) 1128 that allow the user device 104 to communicate with a data store, another computing device or server, user terminals, and/or other devices via the networks 1104, 1106. The user device 104 may also include I/O device(s) 1130, such as a keyboard, a mouse, a pen, a voice input device, a touch input device, a display, speakers, a printer, etc.

Turning to the contents of the memory 1114 in more detail, the memory 1114 may include an operating system 1132 and/or one or more application programs or services for implementing the features disclosed herein including an alarm module 1110(a). In some examples, the alarm module 1110(a) may be configured to provide the alarm graphical user interface 112, schedule alerts, present alerts, and implement the other features described herein. As described in detail with reference to later figures, the wearable device 1108 may include a memory that includes a similar alarm module 1110, which may be accessible by one or more processors of the wearable device 1108. The service provider 1102 may also include a memory that includes an alarm module 1110(b). In this manner, the techniques described herein may be implemented by any one, or a combination of more than one, of the computing devices (e.g., the wearable device 1108, the user device 104, or the service provider 1102).

The service provider computers 1102 may also be any type of computing device such as, but not limited to, a mobile phone, a smartphone, a PDA, a laptop computer, a desktop computer, a thin-client device, a tablet computer, a wearable device, etc. In some examples, the service provider computers 1102 may be in communication with the user device 104 and/or wearable device 1108 via the networks 1104, 1106, or via other network connections.

In one illustrative configuration, the service provider computers 1102 may include at least one memory 1142 and one or more processing units (or processor(s)) 1144. The processor(s) 1144 may be implemented as appropriate in hardware, computer-executable instructions, firmware, or combinations thereof. Computer-executable instruction or firmware implementations of the processor(s) 1144 may include computer-executable or machine-executable instructions written in any suitable programming language to perform the various functions described.

The memory 1142 may store program instructions that are loadable and executable on the processor(s) 1144, as well as data generated during the execution of these programs. Depending on the configuration and type of service provider computer 1102, the memory 1142 may be volatile (such as RAM) and/or non-volatile (such as ROM, flash memory, etc.). The service provider computer 1102 may also include additional removable storage and/or non-removable storage 1146 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1142 may include multiple different types of memory, such as SRAM, DRAM, or ROM. While the volatile memory described herein may be referred to as RAM, any volatile memory that would not maintain data stored therein once unplugged from a host and/or power would be appropriate. The memory 1142 and the additional storage 1146, both removable and non-removable, are both additional examples of non-transitory computer-readable storage media.

The service provider computer 1102 may also contain communications connection(s) 1148 that allow the service provider computer 1102 to communicate with a data store, another computing device or server, user terminals and/or other devices via the networks 1104, 1106. The service provider computer 1102 may also include I/O device(s) 1150, such as a keyboard, a mouse, a pen, a voice input device, a touch input device, a display, speakers, a printer, etc.

Turning to the contents of the memory 1142 in more detail, the memory 1142 may include an operating system 1152 and/or one or more application programs or services for implementing the features disclosed herein including the alarm module 1110(b).

Figure 12:
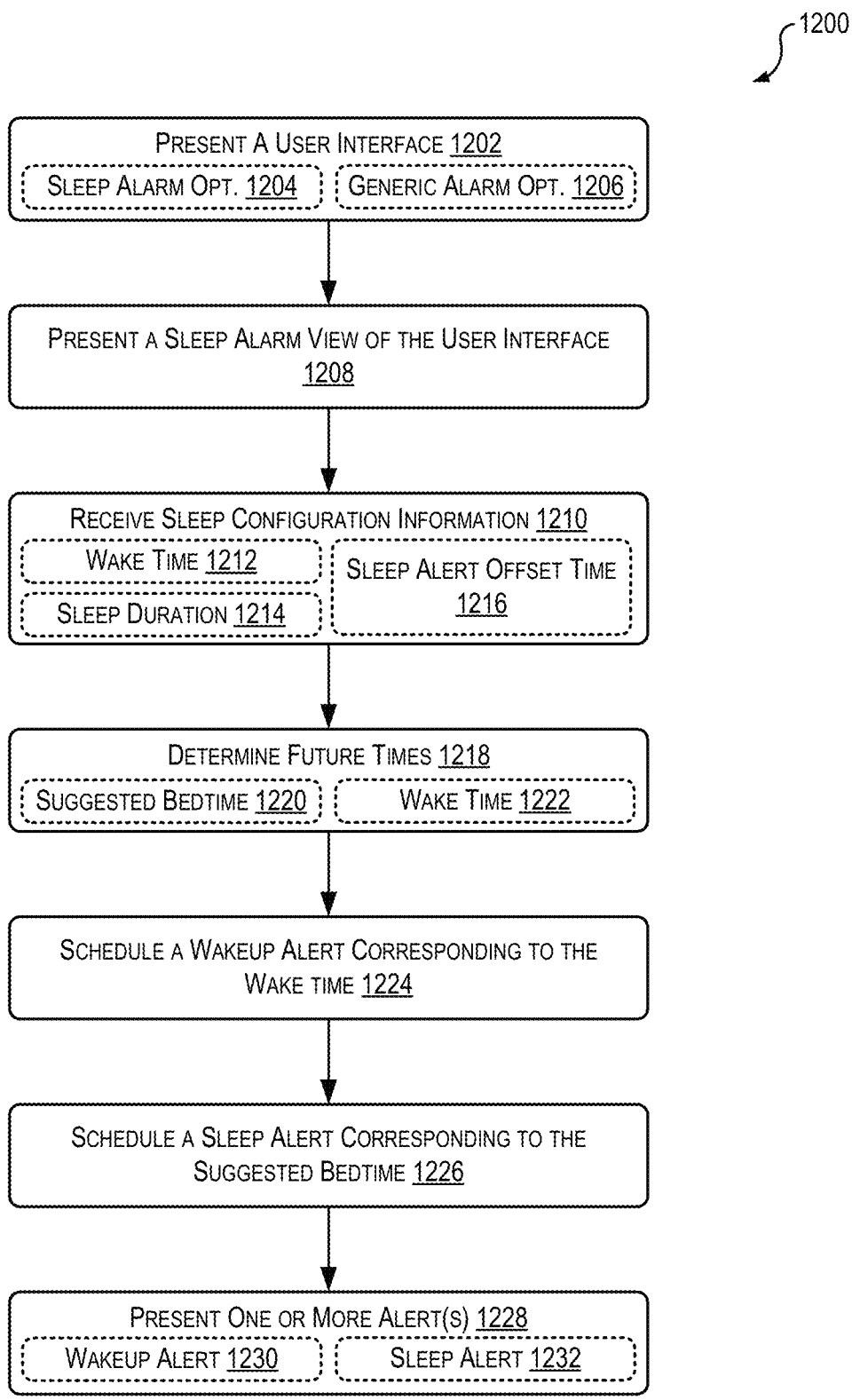
FIG. 12 illustrates a flowchart of a method of interacting with a sleep alarm as described herein, according to at least one example.
Figure 13:
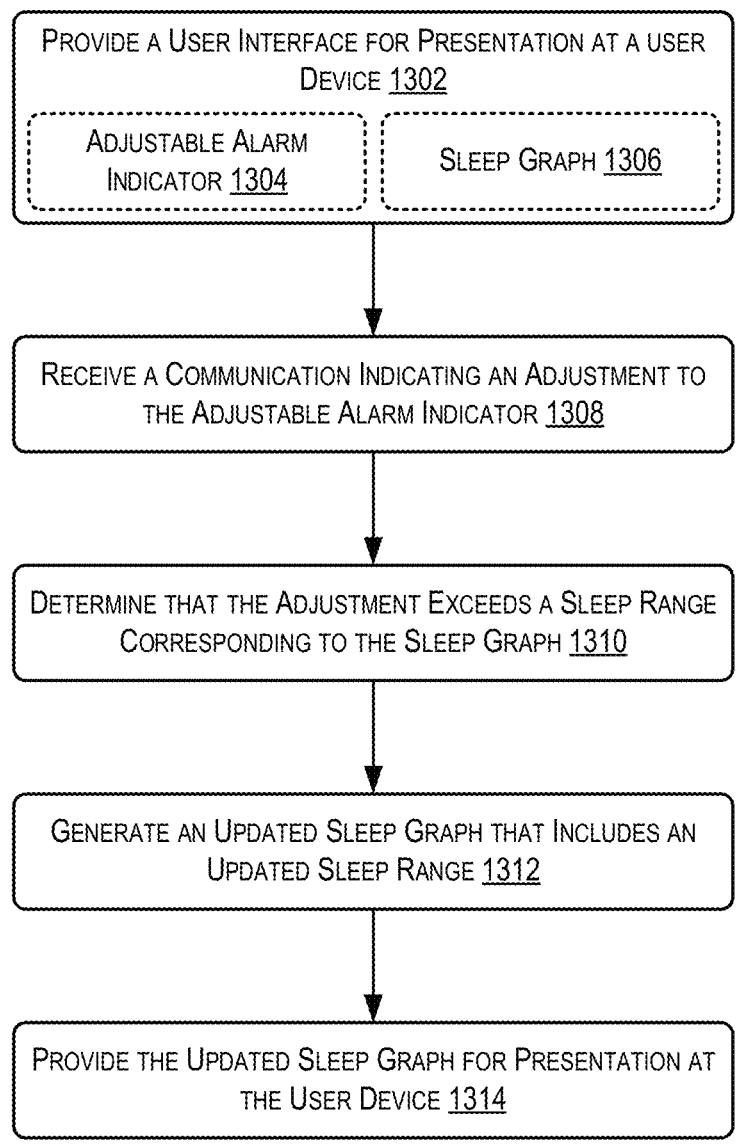
FIG. 13 illustrates a flowchart of a method of interacting with a sleep alarm as described herein, according to at least one example.
Figure 14:
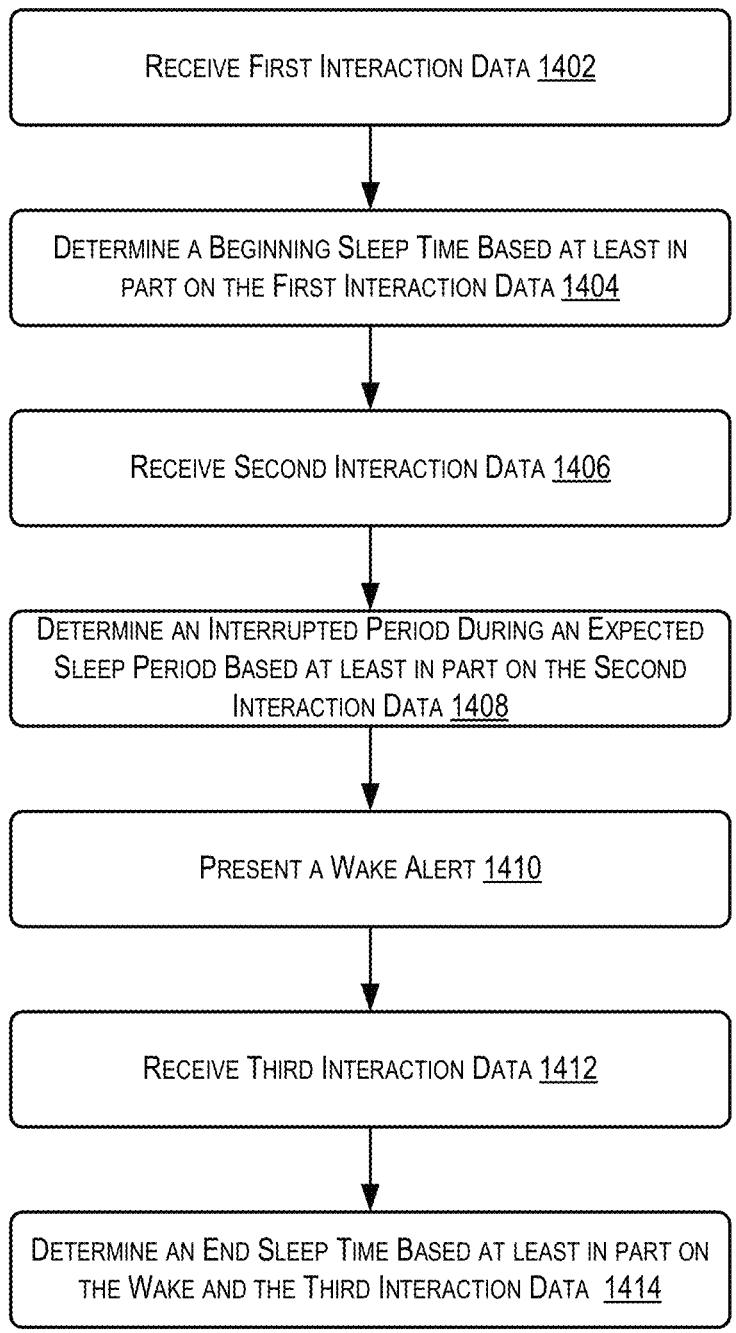
FIG. 14 illustrates a flowchart of a method of interacting with a sleep alarm as described herein, according to at least one example.

FIGS. 12, 13, and 14 illustrate example flow diagrams showing processes 1200, 1300, and 1400 for interacting with sleep alarms, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

FIG. 12 depicts the process 1200 including example acts or techniques relating to interacting with sleep alarms, according to at least one example. The alarm module 1110, whether embodied in the service provider 1102, the wearable device 1108, the user device 104, or any suitable combination of the foregoing may perform the process 1200 of FIG. 12. The process 1200 begins at 1202 by presenting a user interface. The user interface may be presented on a display of a user device. The user interface may be a graphical user interface (e.g., an alarm graphical user interface) and may include one or more interface components for receiving and providing information. For example, the user interface may include components that correspond to a sleep alarm option 1204 and a generic alarm option 1206. Selection of either of the options 1204, 1206 may cause a view of the user interface to be presented. The sleep alarm option 1204 and the generic alarm option 1206 may be presented in connection with other options for accessing other views of the user interface.

At 1208, the process 1200 presents a sleep alarm view of the user interface. The sleep alarm view may be presented in response to selection of the sleep alarm option 1204. Selection of the sleep alarm option 1204 may include a user input the identifies the interface component or selector that corresponds to the sleep alarm option 1204.

At 1210, the process 1200 receives configuration information. The configuration information may be information that configures a sleep alarm. The configuration information may be received as part of a configuration phase of an alarm setting sequence or during a scheduling phase of an alarm setting sequence. In some examples, the configuration information is stored in connection with user settings. The configuration information may also be received in response to one or more user inputs received at the user interface. The user inputs may select, identify, or otherwise input information that configures aspects of the sleep alarm. Examples of configuration information may include a wake time 1212, a sleep duration 1214, and a sleep alert offset time 1216. The wake time 1212 may be a time at which a wakeup alert of the sleep alarm may be presented. The sleep duration 1214 may be a duration of time. The sleep alert offset time 1216 may identify an amount of time prior to the suggested bedtime for a sleep alert. In some examples, other configuration information may be received. For example, other configuration information may identify the days for the sleep alarm to go off, an expected bedtime, aspects of the alerts (e.g., music or sounds, colors, etc.), snooze information, volume adjustment, and/or any other suitable aspect of the sleep alarm. The volume adjustment may function to control the audible volume of alerts presented at a user device independent of a system volume on the user device. In this manner, the volume of alerts of the sleep alarm may be set to a first level and the volume of other alerts, music, and other sounds on the user device may be set to a second, different level.

At 1218, the process 1200 determines future times. Determining the future times may include using at least a portion of the configuration information to compute the future times. The future times may include a suggested bedtime 1220 and a wake time 1222. The wake time 1222 may be the same value as the wake time 1212. In some examples, the wake time 1222 may be determined based at least in part on other configuration information. For example, when the configuration information does not include the wake time 1212, the wake time 1222 may be determined based at least in part on the sleep duration 1214 and the suggested bedtime 1220 or other bedtime. The suggested bedtime 1220 may be determined based at least in part on the wake time 1212 and/or the suggested bedtime 1220 and the sleep duration 1214. For example, if the wake time 1212 was 6:00 am and the sleep duration 1214 was 8 hours, the suggested bedtime 1220 may be 10:00 pm.

At 1224, the process 1200 schedules a wakeup alert corresponding to the wake time. The wakeup alert may be any suitable alert that is set to go off at the wake time. In some examples, scheduling the wakeup alert may include storing information about the wake time in memory of the user device or in any other suitable manner. In some examples, scheduling the wakeup alert activates a do not disturb setting on the user device. The do not disturb setting may remain active at least from a suggested bedtime to the wake time.

At 1226, the process 1200 schedules a sleep alert corresponding to the suggested bedtime. The sleep alert may be any suitable alert that is set to go off at the suggested bedtime or at a time prior to the suggested bedtime corresponding to the sleep alert offset time. For example, the sleep alert may be set to go off prior to the suggested bedtime in order to give the user adequate time to prepare to go to sleep.

At 1228, the process 1200 presents one or more alerts. This may include presenting the one or more alerts on the user device, in any other manner described herein, or in any other suitable manner. The one or more alerts may include the wakeup alert 1230 and the sleep alert 1232, each of which may be presented at different times.

FIG. 13 depicts the process 1300 including example acts or techniques relating to interacting with sleep alarms, according to at least one example. The alarm module 1110, whether embodied in the service provider 1102, the wearable device 1108, the user device 104, or any suitable combination of the foregoing may perform the process 1300 of FIG. 13. The process 1300 begins at 1302 by providing a user interface for presentation at a user device. The user interface may include an adjustable alarm indicator 1304 and a sleep graph 1306. The adjustable alarm indicator 1304 may be an example of the adjustable sleep alarm indicator 122 described herein. The sleep graph 1306 may be an example of the sleep graph 124 described herein. In this manner, the adjustable alarm indicator 1304 may be used to schedule a sleep alert of a sleep alarm, set a bedtime, schedule a wakeup alert of the sleep alarm, and perform any other suitable function. The adjustable alarm indicator 1304 may also provide a graphical representation of the sleep alarm. The sleep graph 1306 may graphical represent a set of sleep data for a certain period.

At 1308, the process 1300 receives a communication indicating an adjustment to the adjustable alarm indicator. The communication may be generated at a user device in response to one or more user inputs at the user interface that adjust the adjustable alarm indicator. The adjustable alarm indicator may include a variable element connecting two ends. Adjusting the adjustable alarm indicator may include moving either end of the adjustable alarm indicator to change the orientation of the variable element and/or change the size of the variable element.

At 1310, the process 1300 determines that the adjustment exceeds a sleep range corresponding to the sleep graph. The adjustment may be the adjustment identified by the communication received at 1308. The sleep range may be initially bounded by a first time and a second time. The first time may correspond to an actual bedtime or a suggested bedtime. The second time may correspond to an actual wake time or an expected wake time. The first time may be the earliest actual bedtime or the earliest suggested bedtime over a particular period. The second time may be the latest actual wake time or the latest expected wake time over the particular period. The adjustment may exceed the sleep range if either one of the elements of the adjustable alarm indicator are moved to a location with respect to the adjustable alarm indicator that corresponds to a suggested bedtime that is earlier than the first time and/or that corresponds to an expected wake time that is later than the second time.

At 1312, the process 1300 generates an updated sleep graph that includes an updated sleep range. The updated sleep range may be enlarged or reduced to include the first time and/or the second time.

At 1314, the process 1300 provides the updated sleep graph for presentation at the user device. This can include providing an updated sleep alarm view of the user interface that includes the updated sleep graph. Once received, the user device may present the updated sleep graph on a display of the user device.

FIG. 14 depicts the process 1400 including example acts or techniques relating to detecting aspects of a sleep cycle, according to at least one example. The alarm module 1110, whether embodied in the service provider 1102, the wearable device 1108, the user device 104, or any suitable combination of the foregoing may perform the process 1400 of FIG. 14. The process 1400 begins at 1402 by receiving first interaction data. The first interaction data may be generated by one or more user devices in response to a user interacting with the one or more user devices. For example, the first interaction data may correspond to the user interacting with one or more applications of a particular user device such as a mobile phone. While the interactions are being detected, it may be determined that the user is awake. In some examples, the first interaction data may simply identify that the user device is in an unlocked state. From this, it may be inferred that the user is interacting with the user device or at least has not locked the user device, and may likely be awake.

At 1404, the process 1400 determines a beginning sleep time based at least in part on the first interaction data. This may include determining, based at least in part on the interaction data, a time when the user ceased interacting with the user device. For example, the interaction data may indicate that the user scheduled an alarm at 10:30 pm, locked the user device, and set the user device down. If the user device remains locked for a certain period of time (e.g., 30 minutes), it may be inferred the user went to bed after setting the user device down (e.g., on a nightstand). As an additional example, the interaction data may indicate that the user was interacting with an application (e.g., a video streaming application) at 11:00 pm, and when the video ended at 11:15 pm, the user device auto locked. From this, it may be inferred that the user went to bed at some point in time between 11:00 pm and 11:15 pm. Other user interaction data may be used to determine an exact time or otherwise an average time may be determined (e.g., 11:07 pm). The beginning sleep time may be stored in a table or other comparable data structure. The beginning sleep time may be used to generate a sleep graph.

At 1406, the process 1400 receives second interaction data. The second interaction data may be received after the beginning sleep time determined at 1404. Thus, the second interaction data may be collected during a time when the user is expected to be asleep. The second interaction data can include any suitable data described herein. For example, the second interaction data may indicate that a flashlight of the user device was turned on at 1:34 am and remained on until 1:45 am. The second interaction data may be collected from a wearable device. For example, the second interaction data may indicate movements and/or interactions of the user during the night while the user wore the wearable device.

At 1408, the process 1400 determines an interrupted period during an expected sleep period based at least in part on the second interaction data. The interrupted period may correspond to a period of time during the night in which the second interaction data indicates the user interacted with the user device, or otherwise moved in a manner indicating a state of being awake. The interrupted period may be stored in a table or other comparable data structure. The interrupted period may be used to generate the sleep graph.

At 1410, the process 1400 presents a wakeup alert. The wakeup alert may be presented in any suitable manner as described herein.

At 1412, the process 1400 receives third interaction data. The third interaction data may be received after the wakeup alert is presented. Thus, the third interaction data may be collected at a time when it is expected that the user will be awake. The third interaction data may include any suitable data as described herein.

At 1414, the process 1400 determines an end sleep time based at least in part on the wakeup alert and the third interaction data. In some examples, the end sleep time may correspond directly to the time at which the wakeup alert was presented. However, in other examples, the end sleep time may take place at a time that is later than the time at which the wakeup alert was presented earlier. This may be because the wakeup alert did not wake up the user or the user snoozed or otherwise turned off the wakeup alert without actually ending her sleep (e.g., getting out of bed) or awake before the wakeup alert. Thus, the techniques described herein may use interaction data collected after the wakeup alert has been presented to identify a more precise end sleep time or wake time.

Figure 15:
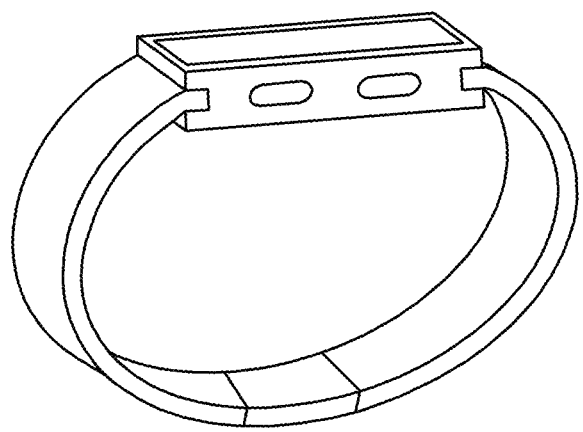
FIG. 15 illustrates an electronic device for interacting with a sleep alarm as described herein, according to at least one example.

Embodiments described herein may take the form of, be incorporated in, or operate with a suitable electronic device. One example of such a device is shown in FIG. 15 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a phone; a tablet computing device; a portable media player; and so on. Still other suitable electronic devices may include laptop/notebook computers, personal digital assistants, touch screens, input-sensitive pads or surfaces, and so on.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

The device may also include one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, the device may include a force sensor to determine an amount of force applied to the cover glass. The force sensor may be a capacitive sensor in some embodiments and a strain sensor in other embodiments. In either embodiment, the force sensor is generally transparent and made from transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic, and/or visual components of the alert may be synchronized to provide an overall experience to a user. One or more components may be delayed relative to other components to create a desired synchronization among them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output, but at a weak or even subliminal level, thereby priming the wearer to receive the auditory output.

Figure 16:
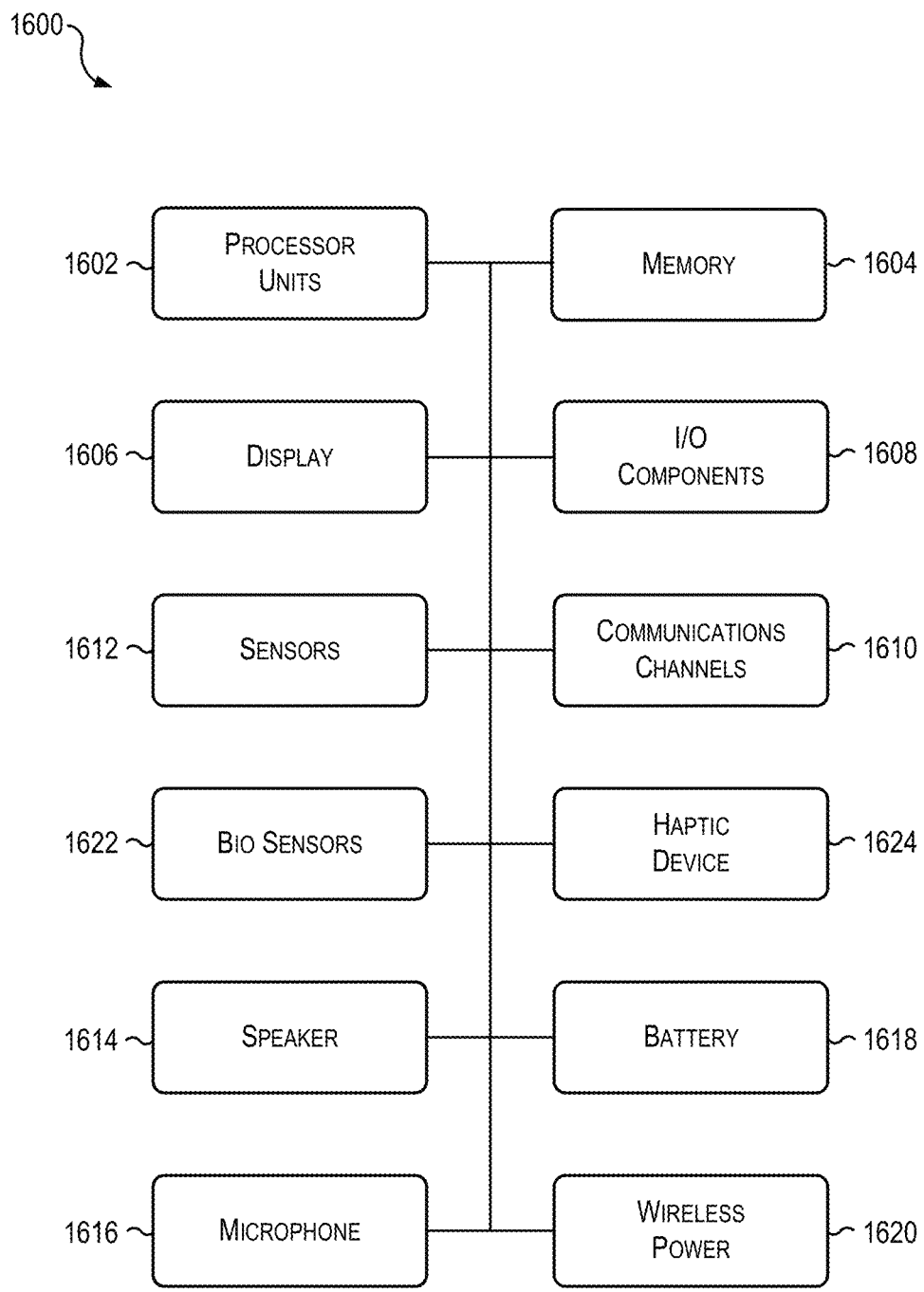
FIG. 16 illustrates a simplified block diagram including components of an example electronic device for interacting with a sleep alarm as described herein, according to at least one example.

FIG. 16 depicts an example schematic diagram of a wearable electronic device 1600. The wearable electronic device 1600 is an example of the wearable device 1108. As shown in FIG. 16, the device 1600 includes one or more processing units 1602 that are configured to access a memory 1604 having instructions stored thereon. The instructions or computer programs may be configured to perform one or more of the operations or functions described with respect to the device 1600 (e.g., an alarm module 1110). For example, the instructions may be configured to control or coordinate the operation of the various components of the device. Such components include, but are not limited to, display 1606, one or more input/output components 1608, one or more communication channels 1610, one or more sensors 1612, a speaker 1614, microphone 1616, a battery 1618, wireless power 1620, bio sensors 1622, and/or one or more haptic feedback devices 1624. In some embodiments the speaker and microphone may be combined into a single unit and/or may share a common port through a housing of the device.

The processing units 1602 of FIG. 16 may be implemented as any electronic device capable of processing, receiving, or transmitting data or instructions. For example, the processing units 1602 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

Figure 17:
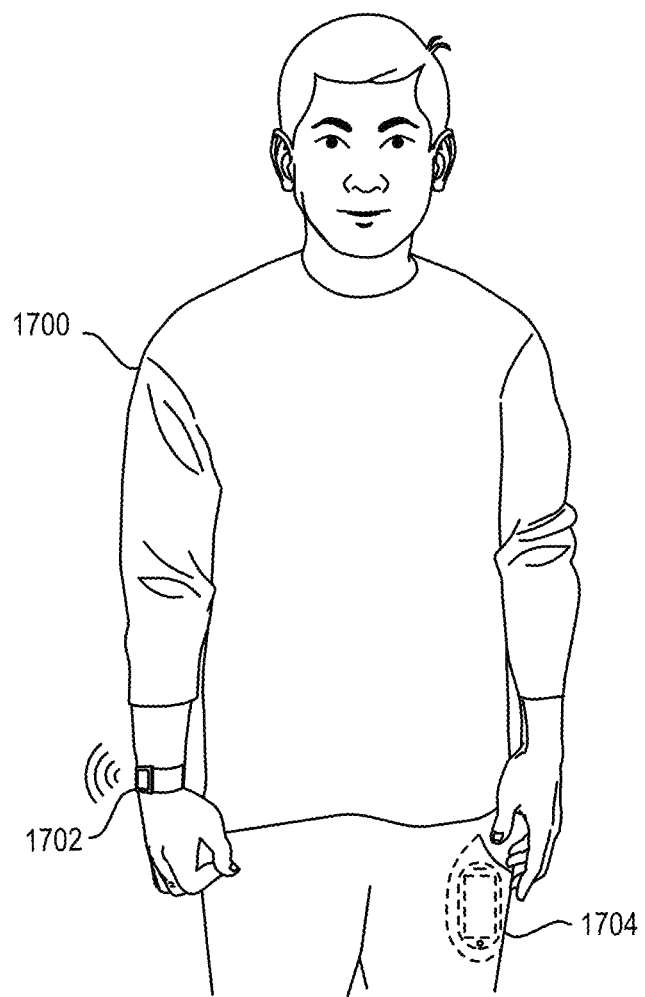
FIG. 17 illustrates a simplified diagram including example electronic devices for interacting with a sleep alarm as described herein, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 17 depicts a user 1700 wearing a first electronic device 1702 with a second electronic device 1704 in his pocket. Data may be wirelessly transmitted between the electronic devices 1702, 1704, thereby permitting the user 1700 to receive, view, and interact with data from the second device 1704 by means of the first electronic device 1702. Thus, the user 1700 may have access to part or all of the second device's functionality through the first electronic device 1702 without actually needing to interact directly with the second device 1704. In some examples, the second electronic device 1704 may be an example of the user device 104. The first electronic device 1702 may be an example of the wearable device 1108.

Further, the electronic devices 1702, 1704 may cooperate not only to share data, but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access, and the like between the two and ultimately to a user. As one non-limiting example, the electronic device 1702 may be unable to place or receive telephone calls while the second device 1704 may be able to do so. A user may nonetheless make and/or receive calls through the first device 1702, which may employ the second device 1704 to actually place or accept a call.

As another non-limiting example, an electronic device 1702 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health data to be provided to a user. In some examples, the sensed biometric data may be used, in part, to determine the historic, current, and/or predicted activity data of the user.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems may also be used (e.g., near field magnetic resonance and radio frequency). Alternatively, the device may also employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based at least in part on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 16, the device 1600 may also include one or more acoustic elements, including a speaker 1614 and/or a microphone 1616. The speaker 1614 may include drive electronics or circuitry and may be configured to produce an audible sound or acoustic signal in response to a command or input. Similarly, the microphone 1616 may also include drive electronics or circuitry and is configured to receive an audible sound or acoustic signal in response to a command or input. The speaker 1614 and the microphone 1616 may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain embodiments of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Figure 18:
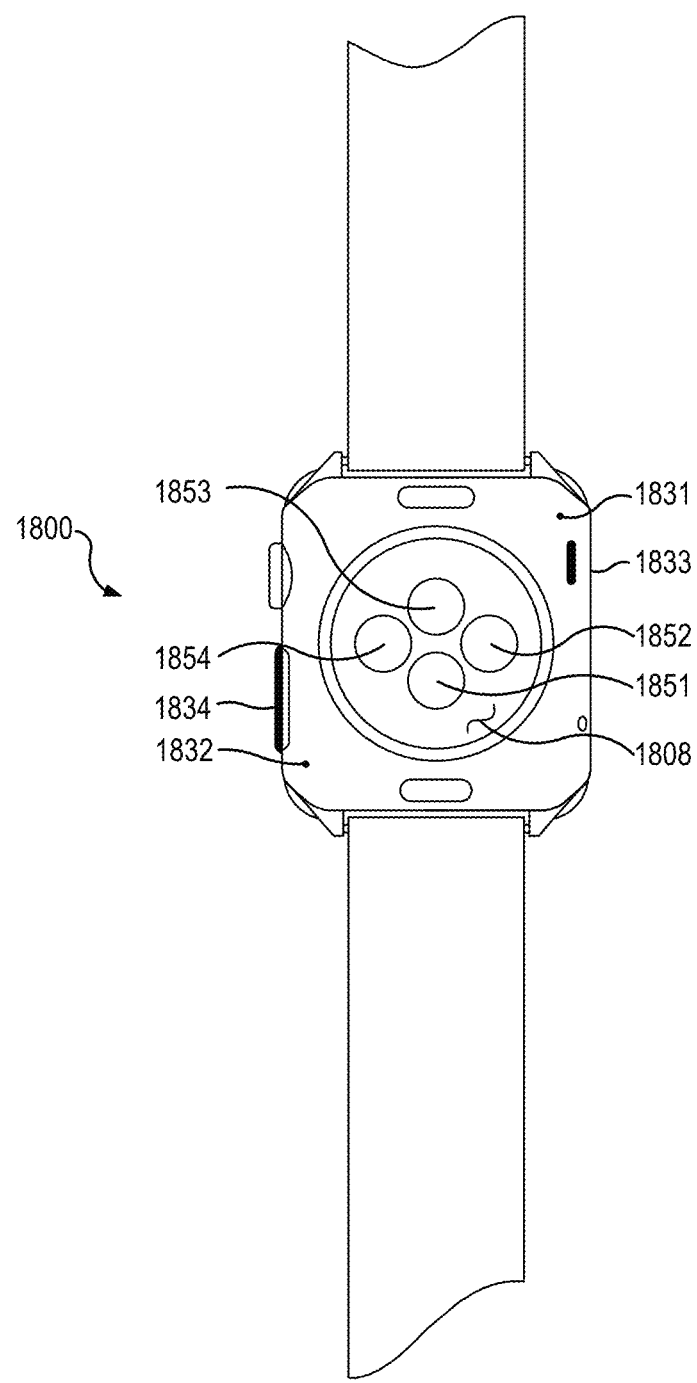
FIG. 18 illustrates an electronic device for interacting with a sleep alarm as described herein, according to at least one example.

FIG. 18 depicts an example electronic device 1800 having one or more biometric sensors. The electronic device 1800 is an example of the wearable device 1108. As shown in FIG. 18, an array of light sources and a photodetector 1851-1854 may be disposed on the rear surface of the device 1800. In one example, the light sources 1851-1853 are formed from light emitting diode (LED) elements that are configured to emit light into a portion of the wearer's body (e.g., wrist). The photodetector 1854 is shared between the multiple light sources 1851-1853 and is configured to receive light reflected from the body. The photodetector may be formed from a photodiode material that is configured to produce a signal based at least in part on the received light. In one implementation, the signal produced by the photodetector 1854 is used to compute a health metric associated with the wearer. In some cases, the light sources 1851-1853 and the photodetector 1854 form a photoplethysmography (PPG) sensor. The first light source 1851 may include, for example, a green LED, which may be adapted for detecting blood perfusion in the body of the wearer. The second light source 1852 may include, for example, an infrared LED, which may be adapted to detect changes in water content or other properties of the body. The third 1853 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 1851-1853 and the photodetector 1854 may also be used for optical data transfer with a base or other device. While FIG. 18 depicts one example embodiment, the number of light sources and/or photodetectors may vary in different embodiments. For example, another embodiment may use more than one photodetector. Another embodiment may also use fewer or more light sources than are depicted in the example of FIG. 18.

Also as shown in FIG. 18, the device 1800 includes multiple electrodes 1831, 1832, 1833, 1834 that are located on or near external surfaces of the device 1800. In the present example, the device 1800 includes a first electrode 1831 and a second electrode 1832 that are located on or proximate to a rear-facing surface of the device body 1810. In this example, the first electrode 1831 and the second electrode 1832 are configured to make electrical contact with the skin of the user wearing the device 1800. In some cases, the first 1831 and second 1832 electrodes are used to take an electrical measurement or receive an electrical signal from the body of the user. As also shown in FIG. 18, the device 1800 may include a third electrode 1833 and a fourth electrode 1834 that are located on or proximate to a perimeter of the case of the device body 1810. In the present example, the third 1833 and fourth 1834 electrodes are configured to be contacted by one or more fingers of the user who is wearing or interacting with the device 1800. In some cases, the third 1833 and fourth 1834 electrodes are also used to take an electrical measurement or receive an electrical signal from the body of the user. In some cases, the first 1831, second 1832, third 1833, and fourth 1834 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 18, the electronic device 1800 includes one or more apertures in the case 1810. A light source 1851-1854 may be disposed in each aperture. In one embodiment, each light source 1851-1853 is implemented as a light-emitting diode (LED). In the present example, the four apertures, three light sources 1851-1853, and a single detector 1854 are used to form one or more sensors. Other embodiments can include any number of light sources. For example, two light sources can be used in some embodiments.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

Illustrative methods and systems for managing user device connections are described above. Some or all of these systems and methods may, but need not, be implemented at least partially by architectures such as those shown at least in FIGS. 1-18. While many of the embodiments are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
    scheduling, using an alarm associated with a first electronic device of a plurality of electronic devices, a sleep alert associated with the alarm;
    scheduling, using the alarm associated with the first electronic device, a wake alert associated with the alarm;
    receiving data from a second electronic device of the plurality of electronic devices, the second electronic device associated with the first electronic device, the data including at least one of interaction data associated with user interactions with the second electronic device or state data associated with a state of the second electronic device;
    determining another electronic device of the plurality of electronic devices at which to have the sleep alert presented based at least in part on the data received from the second electronic device, wherein the another electronic device comprises one of the first electronic device, the second electronic device, or a third electronic device;
    providing information for presenting the sleep alert at the determined another electronic device; and
    providing information for presenting the wake alert at a different electronic device of the plurality of electronic devices, wherein the different electronic device is distinct from the another electronic device and comprises one of the first electronic device, the second electronic device, or the third electronic device.

2. The computer-implemented method of claim 1, wherein the state data comprises power state data or lock state data of the second electronic device.

3. The computer-implemented method of claim 1, wherein the first electronic device, the second electronic device, and the third electronic device are in communication with each other via a local network.

4. The computer-implemented method of claim 1, wherein the another electronic device comprises a network-enabled device in communication with a connected device and configured to adjust one or more aspects of the connected device, and wherein providing the information associated with the sleep alert enables the network-enabled device to adjust the connected device to present the sleep alert.

5. The computer-implemented method of claim 1, wherein scheduling the sleep alert and scheduling the wake alert comprises receiving one or more inputs that adjust one or more variable ends of an adjustable alarm indicator.

6. The computer-implemented method of claim 1, wherein the first electronic device and the second electronic device are associated with a user account.

7. The computer-implemented method of claim 1, wherein the sleep alert is configured for presentation according to a user-configurable amount of time before a scheduled bedtime.

8. The computer-implemented method of claim 1, wherein the sleep alert comprises a bedtime reminder.

9. A user device, comprising:
a memory configured to store computer-executable instructions;
an input component; and
a processor in communication with the memory and configured to execute the computer-executable instructions to perform operations comprising:
receiving, via the input component, a first input that schedules a sleep alert that is associated with an alarm;
receiving, via the input component, a second input that schedules a wake alert that is associated with the alarm;
receiving data from a second electronic device of a plurality of electronic devices, the second electronic device associated with the user device, the data including interaction data associated with user interactions with the second electronic device, wherein the user device is a first electronic device;
determining another electronic device of the plurality of electronic devices at which to have the sleep alert presented based at least in part on the interaction data received from the electronic device, wherein the another electronic device comprises one of the first electronic device, the second electronic device, or a third electronic device;
providing information for presenting the sleep alert at the determined another electronic device; and
providing information for presenting the wake alert at a different electronic device of the plurality of electronic devices, wherein the different electronic device is distinct from the another electronic device and comprises one of the first electronic device, the second electronic device, or the third electronic device.

10. The user device of claim 9, wherein:
the input component comprises a touchscreen display; and
the input comprises a user input at the touchscreen display that adjusts an adjustable alarm indicator associated with the alarm.

11. The user device of claim 9, wherein:
the operations further comprise determining a power state of the second electronic device based at least in part on the data; and
determining the another electronic device is further based at least in part on the power state of the second electronic device.

12. The user device of claim 9, wherein the operations further comprise:
generating a sleep graph based at least in part on the data received from the second electronic device; and
providing other information associated with the sleep graph for presentation at the determined another electronic device.

13. The user device of claim 12, wherein the operations further comprise receiving additional data that comprises additional interaction data from the different electronic device, and wherein generating the sleep graph is further based at least in part on the additional interaction data.

14. The user device of claim 9, wherein providing the information associated with the sleep alert for presentation at the determined another electronic device comprises sending a signal to the determined another electronic device to adjust a connected device that is in communication with the determined another electronic device, the determined another electronic device configured to adjust one or more aspects of the connected device.

15. The user device of claim 9, wherein the user device is a portable user device and the second electronic device comprises a laptop computer, a desktop computer, a sleep monitoring device, a smart outlet and corresponding connected device, a tablet device, a home entertainment device, a smart TV, or a wearable device.

16. One or more computer-readable storage devices comprising computer-executable instructions that, when executed by one or more computer systems, cause the one or more computer systems to perform operations comprising:
receiving information from a first electronic device of a plurality of electronic devices, the information indicating that a sleep alert associated with an alarm been scheduled on the first electronic device;
scheduling, using the alarm associated with the first electronic device, a wake alert associated with the alarm;
receiving data from a second electronic device of the plurality of electronic devices, the second electronic device associated with the first electronic device, the data including at least one of interaction data associated with user interactions with the second electronic device or state data associated with a state of the second electronic device;
determining another electronic device of the plurality of electronic devices at which to have the sleep alert presented based at least in part on the data received from the second electronic device, wherein the another electronic device comprises one of the first electronic device, the second electronic device, or a third electronic device;
providing information for presenting the sleep alert at the determined another electronic device; and
providing information for presenting the wake alert at a different electronic device of the plurality of electronic devices, wherein the different electronic device is distinct from the another electronic device and comprises one of the first electronic device, the second electronic device, or the third electronic device.

17. The one or more computer-readable storage devices of claim 16, wherein the interaction data identifies a time that interactions were logged by the second electronic device and an interaction type.

18. The one or more computer-readable storage devices of claim 16, wherein the operations further comprise:

generating a sleep graph based at least in part on the data; and providing other information associated with the sleep graph for presentation at the first electronic device.

19. The one or more computer-readable storage devices of claim 16, wherein the information enables the determined another electronic device to present the sleep alert in the form of at least one of an auditory alert, a visual alert, or a vibratory alert.

20. The one or more computer-readable storage devices of claim 16, wherein the operations further comprise determining whether a user is asleep based at least in part on the data.

\* \* \* \* \*